United States Patent [19]
Lundquist et al.

[11] Patent Number: 5,409,453
[45] Date of Patent: Apr. 25, 1995

[54] STEERABLE MEDICAL PROBE WITH STYLETS

[75] Inventors: Ingemar H. Lundquist, Oakland; Stuart D. Edwards, Los Altos, both of Calif.

[73] Assignee: Vidamed, Inc., Menlo Park, Calif.

[21] Appl. No.: 109,190

[22] Filed: Aug. 19, 1993

Related U.S. Application Data

[63] Continuation-in-part of Ser. No. 929,638, Aug. 12, 1992, abandoned, Ser. No. 12,370, Feb. 2, 1993, Pat. No. 5,370,675, Ser. No. 62,364, May 13, 1993, Ser. No. 61,647, May 13, 1993, Ser. No. 61,072, May 14, 1993, Pat. No. 5,385,544, and Ser. No. 945,666, Sep. 16, 1992, abandoned.

[51] Int. Cl.$^6$ ............................................. A61B 17/20
[52] U.S. Cl. ................................ 604/22; 128/642; 607/99; 604/280
[58] Field of Search .............. 604/95, 182, 19–22, 604/164, 52, 53, 280; 606/33, 39, 41, 45; 607/101, 105, 99; 128/642, 736

[56] References Cited

U.S. PATENT DOCUMENTS

Re. 32,066  1/1986  Leveen .
5,071,4118 12/1991 Rosenbaum .

(List continued on next page.)

FOREIGN PATENT DOCUMENTS

10858/92  8/1992  Australia .
275632   10/1988  Japan .
2121675   5/1990  Japan .
WO911213  8/1991  WIPO .
WO92/10142 6/1992  WIPO .
9210142   6/1992  WIPO .
WO93/25136 12/1993 WIPO .

OTHER PUBLICATIONS

Standard Urology Product Catalog, Circon ACMI: Stanford (1992).
Chang, Raymond J. et al, American Heart Journal, 125: 1276–1283 (May, 1993).
Cosman, Eric R. et al, Sterostatic and Functional Neurosurgery, pp. 2490–2499 (Date Unknown).
Diasonics, Brochure DIA 2000 171 CRF May. 1988.
Perinchery, Narayan, "Neoplasms of the Prostate Gland." pp. 378–409 (Date Unknown).
Urology 5th ed., Storz, Jan. 1992.
Transuretheral $\mu$wave Thermotherapy for Prostatism:

(List continued on next page.)

Primary Examiner—C. Fred Rosenbaum
Assistant Examiner—Chalin Smith
Attorney, Agent, or Firm—Flehr, Hohbach, Test, Albritton & Herbert

[57] ABSTRACT

A medical probe device for reducing tissue mass in a selected portion of the body comprises a torquable catheter having a control end and a probe end. The probe end includes a stylet guide means with a flexible tip and a tip directing means extending from the control end to the flexible tip for changing the orientation of the central axis of the stylet guide means for directing a flexible stylet outward through the stylet port and through intervening tissue to targeted tissues. A stylet is positioned in the said stylet guide means. The stylet can be an RF electrode, microwave antenna, biopsy means, fluid supply means or combination thereof. Preferably, the stylet is a non-conductive sleeve having an electrode lumen and a second lumen therein, the electrode lumen terminating at a distal port in the distal end of the non-conductive sleeve, a radiofrequency electrode being positioned in said electrode lumen for longitudinal movement therein through the distal port. The medical probe device is particularly useful for removing tissue mass from the prostate and can be used for treating BPH or benign or cancerous tumors of the prostate. The device of this invention can be used in combination with a viewing scope such as a cystoscope, endoscope, laproscope and the like, being sized to extend therethrough or it can include a viewing scope. In one construction, the flexible tip comprises a metal tube with parallel spaced-apart slots extending through the tube to a continuous longitudinal section and enclosed within a flexible sleeve, whereby the tip will preferentially bend in a plane through the axis of the tube and the continuous longitudinal section.

15 Claims, 15 Drawing Sheets

U.S. PATENT DOCUMENTS

| | | |
|---|---|---|
| 1,879,249 | 9/1932 | Hansaker . |
| 1,950,788 | 3/1934 | Ewerhardt et al. . |
| 1,968,997 | 8/1934 | Drucker . |
| 2,008,526 | 7/1935 | Wappler et al. . |
| 2,022,065 | 11/1935 | Wappler . |
| 2,047,535 | 7/1936 | Wappler . |
| 2,118,631 | 5/1938 | Wappler . |
| 2,710,000 | 6/1955 | Cromer et al. . |
| 3,230,957 | 1/1966 | Seifert . |
| 3,339,542 | 9/1967 | Howell . |
| 3,556,079 | 1/1971 | Omizo et al. . |
| 3,595,239 | 7/1971 | Petersen . |
| 3,598,108 | 8/1971 | Jamshidi et al. . |
| 3,682,162 | 8/1972 | Colyer . |
| 3,828,780 | 8/1974 | Morrison, Jr. . |
| 3,835,842 | 9/1974 | Iglesias . |
| 3,840,016 | 10/1974 | Lindemann . |
| 3,850,175 | 11/1974 | Iglesias . |
| 3,858,577 | 1/1975 | Bass et al. . |
| 3,884,237 | 5/1975 | O'Malley et al. . |
| 3,924,628 | 12/1975 | Droegemueller et al. . |
| 3,939,840 | 2/1976 | Storz . |
| 3,942,530 | 3/1976 | Hortheved . |
| 3,948,270 | 4/1976 | Hasson . |
| 3,991,770 | 11/1976 | Leveen . |
| 4,011,872 | 3/1977 | Komiya . |
| 4,119,102 | 10/1978 | Leveen . |
| 4,136,566 | 1/1979 | Christensen . |
| 4,137,920 | 2/1979 | Bonnet . |
| 4,154,246 | 5/1979 | Leveen . |
| 4,204,549 | 5/1980 | Paglione . |
| 4,228,809 | 10/1980 | Paglione . |
| 4,267,828 | 5/1981 | Matsuo . |
| 4,295,467 | 10/1981 | Mann et al. . |
| 4,307,720 | 12/1981 | Weber, Jr. . |
| 4,311,145 | 1/1982 | Esty et al. . |
| 4,311,154 | 1/1982 | Sterzer et al. .......... 128/736 |
| 4,312,364 | 1/1982 | Convert et al. . |
| 4,375,220 | 3/1983 | Matvias . |
| 4,397,314 | 8/1983 | Vaguine . |
| 4,402,311 | 9/1983 | Hattori . |
| 4,405,314 | 9/1983 | Cope . |
| 4,411,266 | 10/1983 | Cosman ................... 606/49 |
| 4,448,198 | 5/1984 | Turner . |
| 4,452,236 | 6/1984 | Utsugi . |
| 4,470,407 | 9/1984 | Hussein . |
| 4,494,539 | 1/1985 | Zenitani et al. . |
| 4,552,554 | 11/1985 | Gould et al. . |
| 4,562,838 | 1/1986 | Walker . |
| 4,565,200 | 1/1986 | Cosman ................... 128/642 |
| 4,568,329 | 2/1986 | Mahurkar . |
| 4,580,551 | 4/1986 | Siegmund et al. . |
| 4,594,074 | 6/1986 | Andersen et al. . |
| 4,601,296 | 7/1986 | Yerushalmi . |
| 4,612,940 | 9/1986 | Kasevich et al. . |
| 4,669,475 | 6/1987 | Turner . |
| 4,672,962 | 6/1987 | Hershenson . |
| 4,676,258 | 6/1987 | Inokuchi et al. . |
| 4,681,122 | 7/1987 | Winters et al. . |
| 4,682,596 | 7/1987 | Bales et al. . |
| 4,697,595 | 10/1987 | Breyer et al. . |
| 4,700,716 | 10/1987 | Kasevich et al. . |
| 4,706,681 | 11/1987 | Breyer et al. . |
| 4,709,698 | 12/1987 | Johnston et al. . |
| 4,719,914 | 1/1988 | Johnson . |
| 4,753,223 | 6/1988 | Bremer ..................... 604/95 |
| 4,765,331 | 8/1988 | Petruzzi et al. . |
| 4,769,005 | 9/1988 | Ginsburg et al. . |
| 4,774,949 | 10/1988 | Fogarty . |
| 4,776,086 | 10/1988 | Kasevich et al. . |
| 4,784,638 | 11/1988 | Ghajar et al. . |
| 4,785,829 | 11/1988 | Convert et al. . |
| 4,798,215 | 1/1989 | Turner . |
| 4,800,899 | 1/1989 | Elliott . |
| 4,805,616 | 2/1989 | Pao . |
| 4,813,429 | 3/1989 | Eshel et al. . |
| 4,817,601 | 4/1989 | Roth et al. . |
| 4,818,954 | 4/1989 | Flachenecker et al. . |
| 4,822,333 | 4/1989 | Lavarenne . |
| 4,823,791 | 4/1989 | D'Amelio et al. . |
| 4,823,812 | 4/1989 | Eshel et al. . |
| 4,860,744 | 8/1989 | Johnson et al. . |
| 4,865,047 | 9/1989 | Chou et al. . |
| 4,872,458 | 10/1989 | Kanehira et al. . |
| 4,887,615 | 12/1989 | Taylor . |
| 4,893,623 | 1/1990 | Rosenbluth . |
| 4,896,671 | 1/1990 | Cunningham et al. . |
| 4,898,577 | 2/1990 | Badger et al. ........... 604/282 |
| 4,905,667 | 3/1990 | Foerster et al. . |
| 4,906,230 | 3/1990 | Maloney et al. ......... 604/95 |
| 4,907,589 | 3/1990 | Cosman ................... 606/34 |
| 4,911,148 | 5/1990 | Sosnowski et al. . |
| 4,911,173 | 3/1990 | Terwilliger . |
| 4,919,129 | 4/1990 | Weber, Jr. et al. . |
| 4,920,978 | 5/1990 | Colvin . |
| 4,932,958 | 6/1990 | Reddy et al. . |
| 4,936,281 | 6/1990 | Stasz . |
| 4,943,290 | 7/1990 | Rexroth . |
| 4,946,449 | 8/1990 | Davis, Jr. . |

| | | |
|---|---|---|
| 4,949,706 | 8/1990 | Thon . |
| 4,950,267 | 8/1990 | Ishihara et al. ............ 606/12 |
| 4,955,377 | 9/1990 | Lennox et al. . |
| 4,961,435 | 10/1990 | Kitagawa et al. . |
| 4,966,597 | 10/1990 | Cosman . |
| 4,967,765 | 11/1990 | Turner et al. . |
| 4,998,932 | 3/1991 | Rosen et al. . |
| 4,998,933 | 3/1991 | Eggers et al. . |
| 5,002,558 | 3/1991 | Klein et al. . |
| 5,007,437 | 4/1991 | Sterzer . |
| 5,007,908 | 4/1991 | Rydell .................... 606/47 |
| 5,010,886 | 4/1991 | Passafaro et al. . |
| 5,026,959 | 6/1991 | Ito et al. . |
| 5,029,588 | 7/1991 | Yock et al. . |
| 5,030,227 | 7/1991 | Rosenbluth et al. . |
| 5,035,695 | 7/1991 | Weber, Jr. et al. . |
| 5,035,696 | 7/1991 | Rydell . |
| 5,057,105 | 10/1991 | Malone et al. . |
| 5,057,106 | 10/1991 | Kasevich et al. . |
| 5,059,851 | 10/1991 | Corl et al. . |
| 5,080,660 | 1/1992 | Buelna . |
| 5,083,565 | 1/1992 | Parins . |
| 5,084,044 | 1/1992 | Quint . |
| 5,100,423 | 3/1992 | Fearnot . |
| 5,108,415 | 4/1992 | Pinchuk et al. . |
| 5,109,859 | 5/1992 | Jenkins . |
| 5,116,615 | 5/1992 | Gokcen et al. . |
| 5,120,316 | 6/1992 | Morales et al. . |
| 5,122,137 | 6/1992 | Lennox . |
| 5,135,525 | 8/1992 | Biscoping et al. . |
| 5,150,717 | 9/1992 | Rosen et al. . |
| 5,170,787 | 12/1992 | Lindegren . |
| 5,178,620 | 1/1993 | Eggers et al. . |
| 5,179,962 | 1/1993 | Dutcher et al. . |
| 5,190,539 | 3/1993 | Fletcher et al. . |
| 5,195,965 | 3/1993 | Shantha . |
| 5,197,963 | 3/1993 | Parins .................... 606/46 |
| 5,201,732 | 4/1993 | Parins et al. . |
| 5,220,927 | 6/1993 | Astrahan et al. ........ 128/736 |
| 5,228,441 | 7/1993 | Lundquist . |
| 5,234,004 | 8/1993 | Hascoet et al. ........ 607/116 |
| 5,235,964 | 8/1993 | Abenaim . |
| 5,249,585 | 10/1993 | Turner et al. ............ 607/99 |
| 5,257,451 | 11/1993 | Edwards et al. . |
| 5,281,218 | 1/1994 | Imran . |
| 5,300,069 | 4/1994 | Hunsberger et al. . |
| 5,300,099 | 4/1994 | Rudie . |
| 5,322,064 | 6/1994 | Lundquist . |

OTHER PUBLICATIONS

Early Mayo Foundation Experience: Blute, Mayo Clinic Proceedings: vol. 67 May 92 pp. 417–421.

New Therapies for Benign Prostatic Hyperplasia, Editorial Bruskewitz, Mayo Clinic Proceedings vol. 67 May 92 pp. 493–495.

Industry Strategies, Urology: "A Multi Billion Dollar Market . . . " Stephen Scala Nov. 19, 1991 pp. 1–32.

U.I. Dept. of Health and Human Services, MMWR 41: 401–404 vol. 41, No. 23, (Jun. 12, 1992).

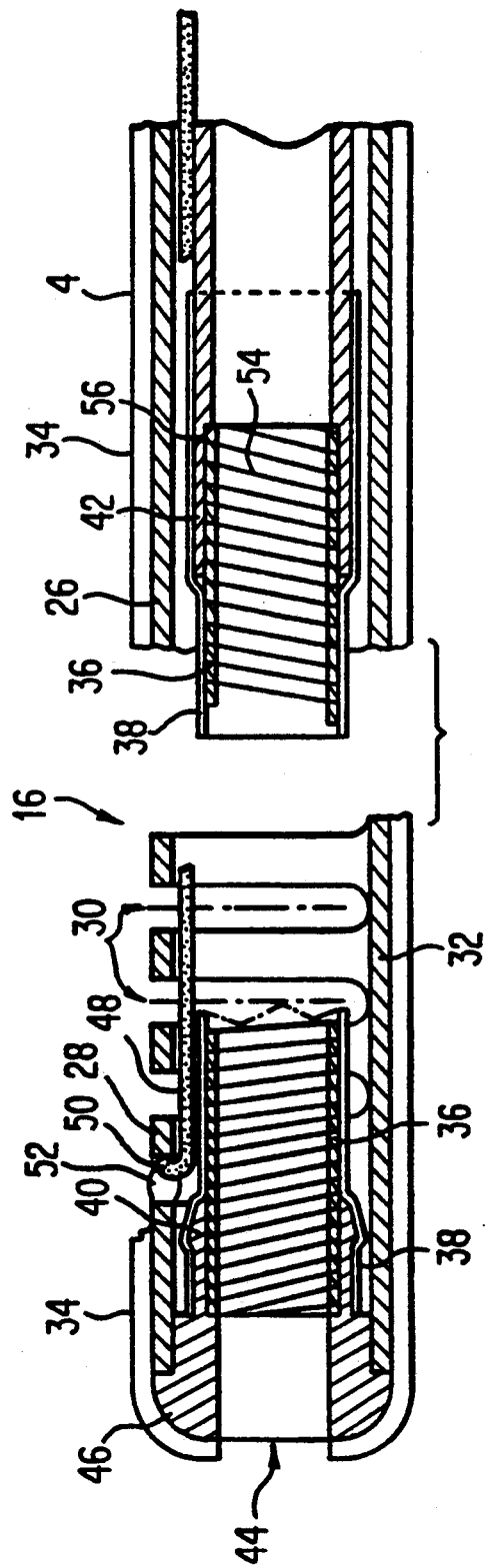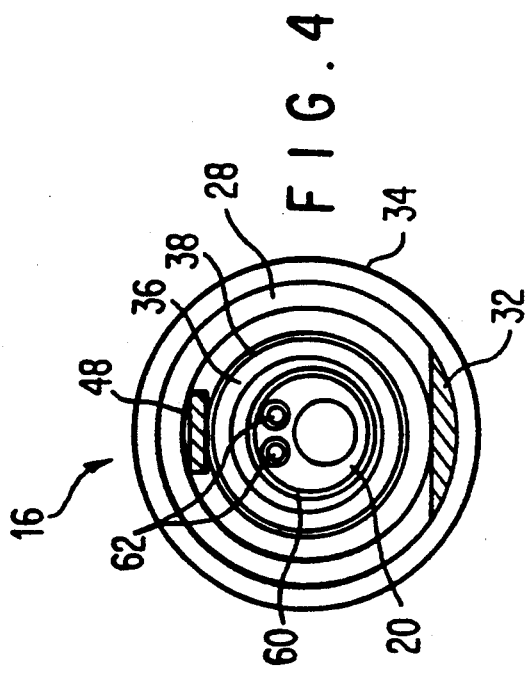

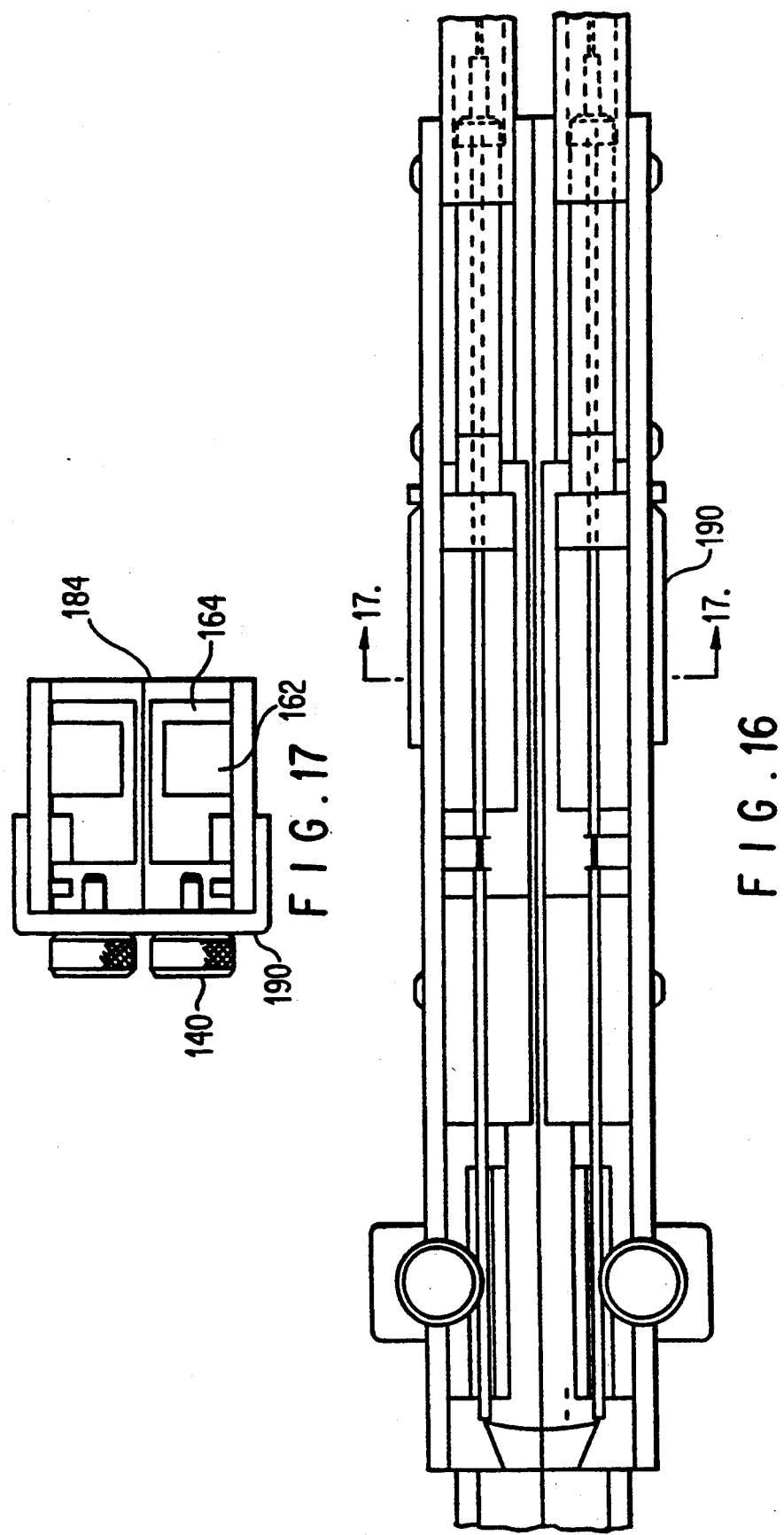

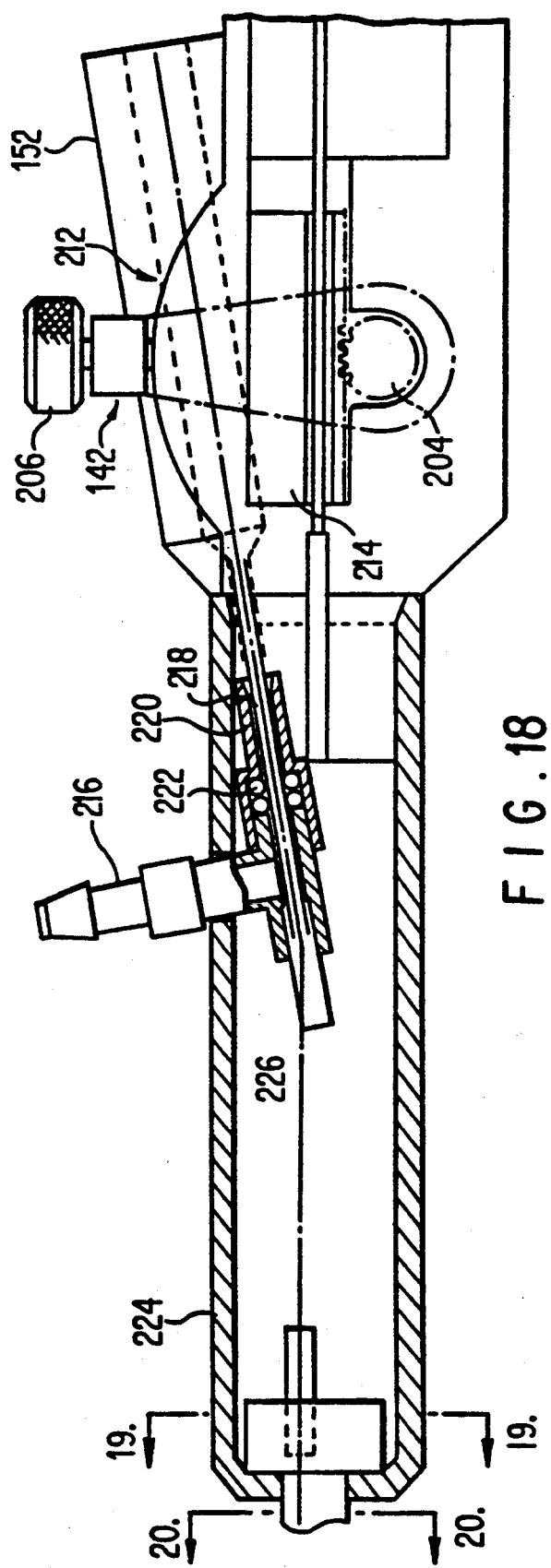
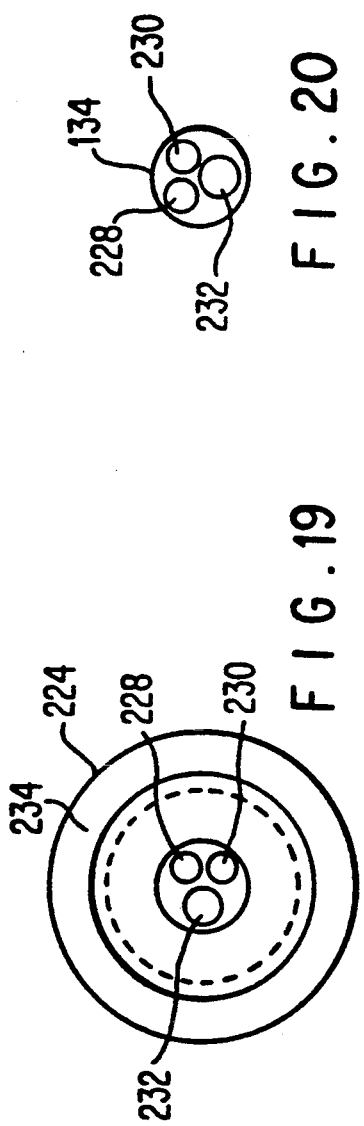
FIG. 18
FIG. 19
FIG. 20

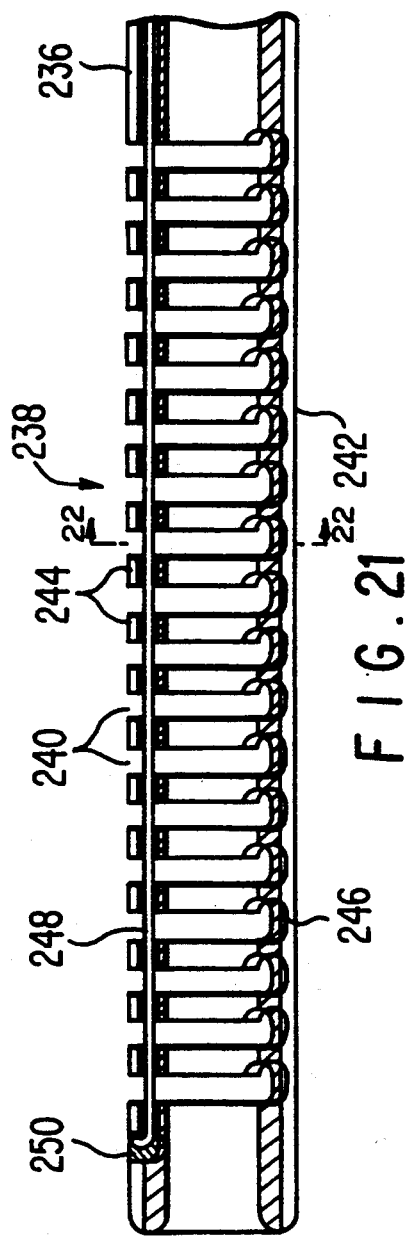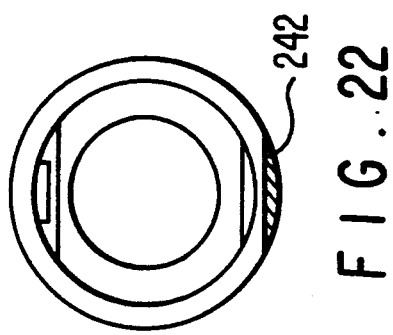

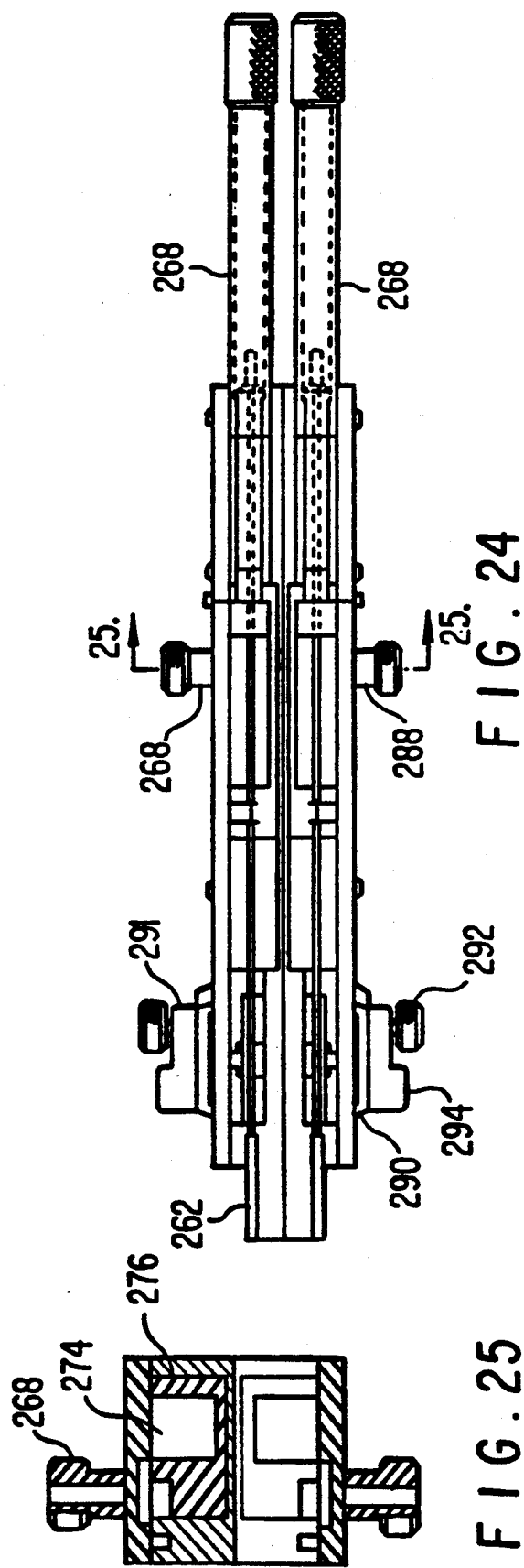

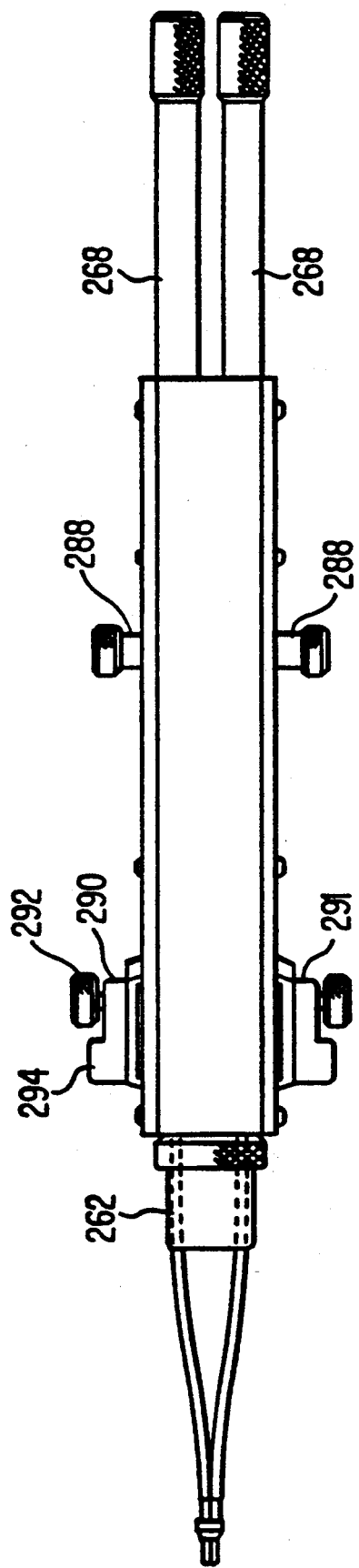
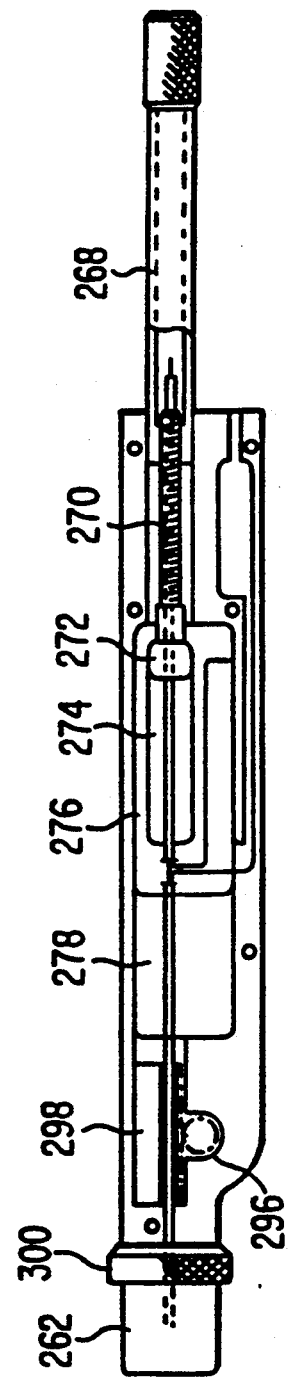
FIG. 26
FIG. 27

STEERABLE MEDICAL PROBE WITH STYLETS

RELATIONSHIP TO COPENDING APPLICATION

This application is a continuation-in-part of applications Ser. No. 07/929,638, filed Aug. 12, 1994, now abandoned, Ser. No. 08/012,370, filed Feb. 2, 1993, now U.S. Pat. No. 5,370,675, Ser. No. 08/062,364, filed May 13, 1993, pending Ser. No. 08/061,647, filed May 13, 1993, Ser. No. 08/061,647, filed May 14, 1993, and Ser. No. 07/945,666, now abandoned. The entire contents of the above application are hereby incorporated by reference.

FIELD OF THE INVENTION

This invention is directed to a unique device and method for penetrating body tissues for medical purposes such as reducing the mass of selected tissues by therapeutic ablation and fluid substance delivery, for example. The device penetrates tissue to the precise target selected in order to deliver energy to the tissue and/or deliver substances. It limits this treatment to the precise preselected site, thereby minimizing trauma to normal surrounding tissue and achieving a greater medical benefit. This device is a cannula-like device for positioning a treatment assembly in the area or organ selected for medical treatment with one or more stylets in the cannula, mounted for extension from a stylet port in the side of the cannula through surrounding tissue to the tissue targeted for medical intervention.

BACKGROUND OF THE INVENTION

Treatment of cellular tissues usually requires direct contact of target tissue with a medical instrument, usually by surgical procedures exposing both the target and intervening tissue to substantial trauma. Often, precise placement of a treatment probe is difficult because of the location of targeted tissues in the body or the proximity of the target tissue to easily damaged, critical body organs, nerves, or other components.

Benign prostatic hypertrophy or hyperplasia (BPH), for example, is one of the most common medical problems experienced by men over 50 years old. Urinary tract obstruction due to prostatic hyperplasia has been recognized since the earliest days of medicine. Hyperplastic enlargement of the prostate gland often leads to compression of the urethra, resulting in obstruction of the urinary tract and the subsequent development of symptoms including frequent urination, decrease in urinary flow, nocturia, pain, discomfort, and dribbling. The association of BPH with aging has been shown to exceed 50% in men over 50 years of age and increases in incidence to over 75% in men over 80 years of age. Symptoms of urinary obstruction occur most frequently between the ages of 65 and 70 when approximately 65% of men in this age group have prostatic enlargement.

Currently there is no proven effective nonsurgical method of treatment of BPH. In addition, the surgical procedures available are not totally satisfactory. Currently patients suffering from the obstructive symptoms of this disease are provided with few options: continue to cope with the symptoms (i.e., conservative management), submit to drug therapy at early stages, or submit to surgical intervention. More than 430,000 patients per year undergo surgery for removal of prostatic tissue in the United States. These represent less than five percent of men exhibiting clinical significant symptoms.

Those suffering from BPH are often elderly men, many with additional health problems which increase the risk of surgical procedures. Surgical procedures for the removal of prostatic tissue are associated 12 with a number of hazards including anesthesia related morbidity, hemorrhage, coagulopathies, pulmonary emboli and electrolyte imbalances. These procedures performed currently can also lead to cardiac complications, bladder perforation, incontinence, infection, urethral or bladder neck stricture, retention of prostatic chips, retrograde ejaculation, and infertility. Due to the extensive invasive nature of the current treatment options for obstructive uropathy, the majority of patients delay definitive treatment of their condition. This circumstance can lead to serious damage to structures secondary to the obstructive lesion in the prostate (bladder hypertrophy, hydronephrosis, dilation of the kidney pelves, chronic infection, dilation of ureters, etc.) which is not without significant consequences. In addition, a significant number of patients with symptoms sufficiently severe to warrant surgical intervention are therefore poor operative risks and are poor candidates for prostatectomy. In addition, younger men suffering from BPH who do not desire to risk complications such as infertility are often forced to avoid surgical intervention. Thus the need, importance and value of improved surgical and non-surgical methods for treating BPH is unquestionable.

High-frequency currents are used in electrocautery procedures for cutting human tissue especially when a bloodless incision is desired or when the operating site is not accessible with a normal scalpel but presents an access for a thin instrument through natural body openings such as the esophagus, intestines or urethra. Examples include the removal of prostatic adenomas, bladder tumors or intestinal polyps. In such cases, the high-frequency current is fed by a surgical probe into the tissue to be cut. The resulting dissipated heat causes boiling and vaporization of the cell fluid at this point, whereupon the cell walls rupture and the tissue is separated.

Destruction of cellular tissues in situ has been used in the treatment of many diseases and medical conditions alone or as an adjunct to surgical removal procedures. It is often less traumatic than surgical procedures and may be the only alternative where other procedures are unsafe. Ablative treatment devices have the advantage of using an electromagnetic energy which is rapidly dissipated and reduced to a nondestructive level by conduction and convection forces of circulating fluids and other natural body processes.

Microwave, radiofrequency, acoustical (ultrasound) and light energy (laser) devices, and tissue destructive substances have been used to destroy malignant, benign and other types of cells and tissues from a wide variety of anatomic sites and organs. Tissues treated include isolated carcinoma masses and, more specifically, organs such as the prostate, glandular and stromal nodules characteristic of benign prostate hyperplasia. These devices typically include a catheter or cannula which is used to carry a radiofrequency electrode or microwave antenna through a duct to the zone of treatment and apply energy diffusely through the duct wall into the surrounding tissue in all directions. Severe trauma is often sustained by the duct wall during this cellular destruction process, and some devices combine cooling systems with microwave antennas to reduce trauma to the ductal wall. For treating the prostate with these devices, for example, heat energy is delivered through the walls of the urethra into the surrounding prostate cells in an effort to ablate the tissue causing the constriction of the urethra. Light energy, typically from a laser, is delivered to prostate tissue target sites by "burning through" the wall of the urethra. Healthy cells of the duct wall and healthy tissue between the nodules and duct wall are also indiscriminately destroyed in the process and can cause unnecessary loss of some prostate function. Furthermore, the added cooling function of some microwave devices complicates the apparatus and requires that the device be sufficiently large to accommodate this cooling system.

Application of liquids to specific tissues for medical purposes is limited by the ability to obtain delivery without traumatizing intervening tissue and to effect a delivery limited to the specific target tissue. Localized chemotherapy, drug infusions, collagen injections, or injections of agents which are then activated by light, heat or chemicals would be greatly facilitated by a device which could conveniently and precisely place a fluid (liquid or gas) supply cannula opening at the specific target tissue.

OBJECTS AND SUMMARY OF THE INVENTION

It is an object of this invention to provide a device and method for penetrating tissue, through intervening tissues to the precise target tissue selected for a medical action such as tissue ablation and/or substance delivery, limiting this activity to the precise preselected site, and thereby minimizing the trauma and achieving a greater medical benefit.

It is another object of this invention to provide a device and method for tissue ablation of body tissues which delivers the therapeutic energy directly into targeted tissues while minimizing effects on its surrounding tissue.

It is a still further object of this invention to provide a device and method for introducing fluid treatment agents such as flowable liquids and gases, with greater precision and ease to a specific location in the body.

Another object of this invention is to provide a thermal destruction device which gives the operator more information about the temperature and other conditions created in both the tissue targeted for treatment and the surrounding tissue. In addition, it will provide more control over the physical placement of the stylet and over the parameters of the tissue ablation process.

In summary, the medical probe device of this invention for reducing tissue mass in a selected portion of the body comprises a torquable catheter having a control end and a probe end. The probe end includes a stylet guide means with a flexible tip and a tip directing means extending from the control end to the flexible tip for changing the orientation of the central axis of the stylet guide means for directing a flexible stylet outward through the stylet port and through intervening tissue to targeted tissues. A stylet is positioned in the said stylet guide means and serves as an RF electrode. Preferably, the stylet is a non-conductive sleeve having an electrode lumen and a second lumen therein, the electrode lumen terminating at a distal port in the distal end of the non-conductive sleeve, a radiofrequency electrode being positioned in said electrode lumen for longitudinal movement therein through the distal port.

In one embodiment, the radiofrequency electrode and at least one portion of an opposed surface of the electrode lumen and the electrode surface are spaced apart to define a liquid supply passageway for delivery of medicament liquid. The second lumen can be a fluid supply lumen terminating at a distal port in the distal end of the non-conductive sleeve or it can be temperature sensor lumen terminating adjacent the distal end of the non-conductive sleeve, at least one temperature sensing device being positioned in the temperature sensor lumen. The temperature sensing device can be a thermocouple positioned near the distal end of the non-conductive sleeve, the electrical leads of which extend through the temperature sensor lumen.

A preferred embodiment includes two temperature sensing devices positioned in the temperature sensor lumen, one temperature sensing device being positioned within about 1 mm of the distal end of the non-conductive sleeve, and the second temperature sensing device being positioned at least about 3 mm from the distal end of the non-conductive sleeve. In that event, the temperature sensing devices can both be thermocouples, the electrical leads of which extend through the second lumen.

In one embodiment, the non-conductive sleeve includes at least an electrode lumen, a temperature sensor lumen, and a fluid delivery lumen, the electrode lumen terminating at a distal port in the distal end of the non-conductive sleeve, a radiofrequency electrode being positioned in said electrode lumen for longitudinal movement therein through the distal port, the fluid delivery lumen terminating at a distal port in the distal end of the non-conductive sleeve, and the temperature sensor lumen terminating adjacent the distal end of the non-conductive sleeve, at least one temperature sensing device positioned in the temperature sensor lumen.

The medical probe device is particularly useful for removing tissue mass from the prostate and can be used for treating BPH or benign or cancerous tumors of the prostate.

In one construction, the flexible tip comprises a metal tube with parallel spaced-apart slots extending through the tube to a continuous longitudinal section and enclosed within a flexible sleeve, whereby the tip will preferentially bend in a plane through the axis of the tube and the continuous longitudinal section.

The device of this invention can be used in combination with a viewing scope such as a cystoscope, endoscope, laproscope and the like, being sized to extend therethrough.

Alternatively, the device can include a viewing scope, the catheter enclosing a fiber optic, and the control end includes an optic viewing means connected to the fiber optic.

BRIEF DESCRIPTION OF THE DRAWINGS

FIG. 3 is an enlarged cross-sectional view of the cannula shown in FIG. 2, with the outer insulating cover removed.

FIG. 4 is a cross-sectional view of the cannula shown in FIG. 2, taken along the line 4—4 of FIG. 2.

FIG. 16 is a top plan view of the control handle for the ablation device of FIG. 13.

FIG. 17 is a cross-sectional view of the control handle of FIG. 16, taken along the line 17—17 of FIG. 16.

FIG. 18 is an enlarged cross-sectional side view of the optics assembly of the ablation device of FIG. 13 with a flushing liquid connector.

FIG. 19 is a cross-sectional view of the distal end of the handle shown in FIG. 18, taken along the line 19—19 of FIG. 18.

FIG. 20 is a cross-sectional view of the cannula shown in FIG. 18, taken along the line 20—20 of FIG 18.

FIG. 21 is a side elevational view in section of an alternate torque tube assembly without the insulating outer cover.

FIG. 22 is a cross-sectional view of the torque tube shown in FIG. 21 taken along the line 22—22 of FIG. 21.

FIG. 24 is a top plan view of the embodiment shown in FIG. 23.

FIG. 25 is a cross-sectional view taken along the line 25—25 of FIG. 24.

FIG. 26 is a bottom plan view of the embodiment shown in FIG. 23.

FIG. 27 is a side elevational view partially in section of the handle shown in FIG. 23 showing its principal internal components.

DETAILED DESCRIPTION OF THE INVENTION

Figure 1:
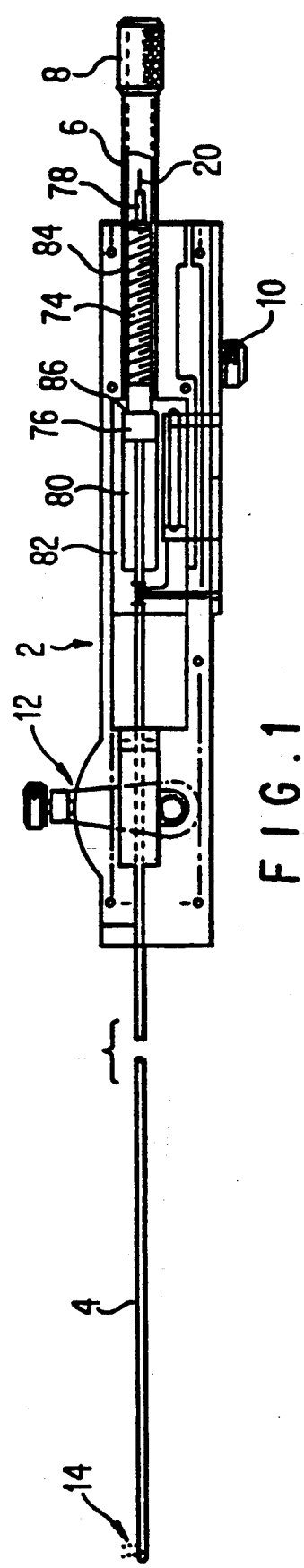
FIG. 1 is side view of an ablation device of this invention for use with a cystoscope.

The device of this invention provides a precise controlled positioning of a treatment stylet in a tissue targeted for treatment, destruction or sampling from a cannula positioned in the vicinity of the target tissue.

The term "stylet" as used hereinafter is defined to include both solid and hollow probes which are adapted to be passed from a cannula port through normal tissue to targeted tissues. The stylet is shaped to facilitate easy passage through tissue. It can be a solid wire, thin rod, or other solid shape or it can be a thin hollow tube or other shape having a longitudinal lumen for introducing fluids to or removing materials from a site. The stylet can also be a thin hollow tube or other hollow shape, the hollow lumen thereof containing a reinforcing or functional rod. The stylet preferably has a sharpened end to reduce resistance and trauma when it is pushed through tissue to a target site.

The stylet can be designed to provide a variety of medically desired treatments of a selected tissue. As a radiofrequency electrode, it can be used to ablate or destroy targeted tissues. As a hollow tube, it can be used to deliver a treatment fluid such as a liquid to targeted tissues. The liquid can be a simple solution or a suspension of solids, for example, colloidal particles, in a liquid. Since the stylet is very thin, it can be directed from the cannula through intervening normal tissue with a minimum of trauma to the normal tissue.

The device and method of this invention provide a more precise, controlled medical treatment which is suitable for destroying cells of medically targeted tissues throughout the body, both within and external to body organs. The device and method are particularly useful for treating benign prostate hyperplasia (BPH), and the device and its use are hereinafter described with respect to BPH, for purposes of simplifying the description thereof. It will be readily apparent to a person skilled in the art that the device and method can be used to destroy body tissues in any body cavities or tissue locations that are accessible by percutaneous or endoscopic catheters, and is not limited to the prostate. Application of the device and method in all of these organs and tissues are intended to be included within the scope of this invention.

BPH is a condition which arises from the replication and growth of cells in the prostate and the decrease of cell death rate, forming glandular and stromal nodules which expand the prostate and constrict the opening of the prostatic urethra. Glandular nodules are primarily concentrated within the transition zone, and stromal nodules within the periurethral region. Traditional treatments of this condition have included surgical removal of the entire prostate gland, digital removal of the adenoma, as well as transurethral resection of the urethral canal and prostate to remove tissue and widen the passageway. One significant and serious complication associated with these procedures is iatrogenic sterility. More recently, laser treatment has been employed to remove tissue, limiting bleeding and loss of body fluids. Balloons have also been expanded within the urethra to enlarge its diameter, with and without heat, but have been found to have significant limitations.

Microwave therapy has been utilized with some success by positioning a microwave antenna within the prostatic urethra and generating heat in the tissue surrounding the urethra with an electromagnetic field. Coolants are sometimes applied within the catheter shaft to reduce the temperature of the urethral wall. This necessitates complicated mechanisms to provide both cooling of the immediately adjacent tissues while generating heat in the more distant prostatic tissue. This technique is similar to microwave hyperthermia. Similarly, radiofrequency tissue ablation with electrodes positioned within the urethra exposes the urethral wall to destructive temperatures. To avoid this, low temperature settings required to protect the urethra must be so low that the treatment time required to produce any useful effect is unduly extended, e.g. up to three hours of energy application.

One embodiment of the device of this invention uses the urethra to access the prostate and positions RF electrode stylets directly into the tissues to be destroyed. The portion of the stylet conductor extending from the urethra to targeted tissues is enclosed within a longitudinally adjustable sleeve shield which prevents exposure of the tissue adjacent to the sleeve to the RF current. The sleeve movement is also used to control the amount of energy per unit surface area which is delivered by controlling the amount of electrode exposed. Thus the ablative destruction is confined to the tissues targeted for destruction, namely those causing the constriction. Other aspects of the invention will become apparent from the drawings and accompanying descriptions of the device and method of this invention. It will be readily apparent to a person skilled in the art that this procedure can be used in many areas of the body for percutaneous approaches and approaches through body orifices.

Further details about the preferred embodiments of the invention will become evident in conjunction with the description of the drawings.

FIG. 1 is a side view of an ablation device of this invention for use with a cystoscope. The control handle 2 supports a flexible ablation cannula 4 extending in the distal direction therefrom. A manual electrode control rod 6 with a knurled tip 8 extends from the handle 2 in the proximal direction for advancing and retracting the RF electrode component of the stylet as will be described in greater detail hereinafter. Manual stylet control knob 10 extends from the bottom of handle advance and retract the stylet as described in greater detail hereinafter. A cannula tip deployment lever 12 is mounted on the top of the handle 2. The distal tip 14 of the cannula is flexible. Movement of the lever 12 in the proximal direction (to the right in the figure, toward the user) deploys the tip 14 in a direction which is off-axis from the central axis of the cannula.

Figure 2:
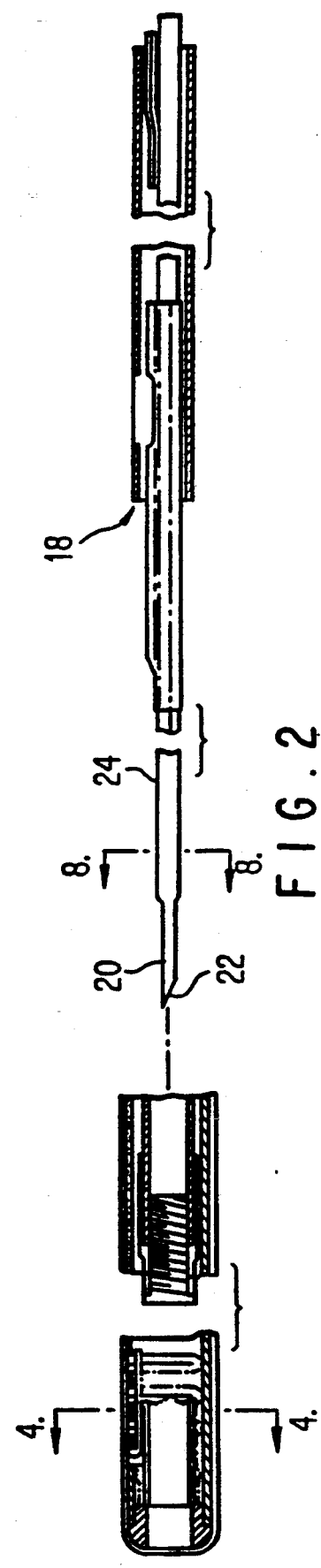
FIG. 2 is a cross-sectional view of the cannula and stylet portion of the ablation device of FIG. 1.

FIG. 2 is a cross-sectional view of the distal end of the cannula and stylet portion of the ablation device of FIG. 1. The distal tip comprises an outer flexible tube construction 16 and a stylet 18 which extends and can be advanced therethrough. The stylet 18 can comprise an RF electrode 20 with a sharpened tip 22 for penetrating tissue and an insulating sleeve 24 through which it can be extended and retracted. The stylet construction is described in greater detail in copending application Ser. No. 08/061,647, filed May 13, 1993, the entire contents of which are hereby incorporated by reference.

Figure 5:
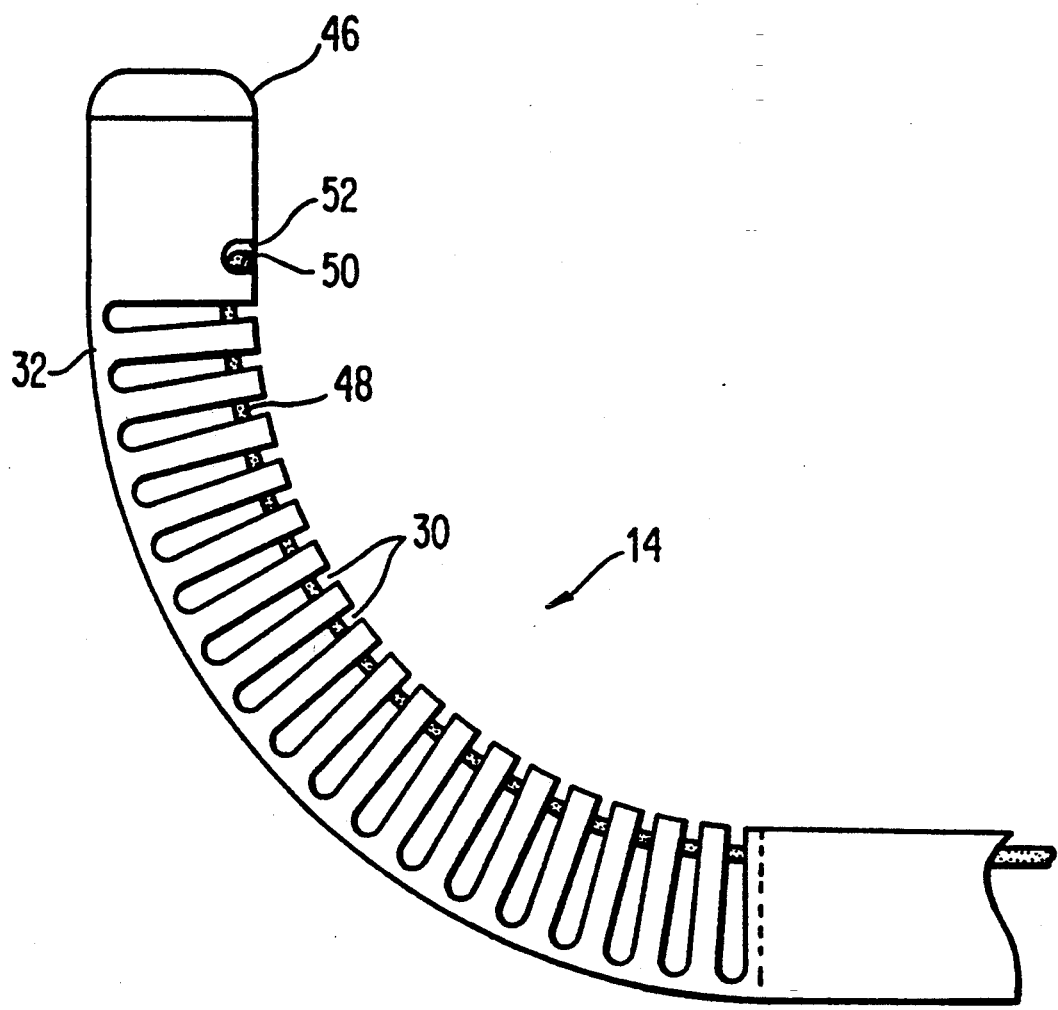
FIG. 5 is a side elevational view of the torque tube component of the cannula shown in FIG. 3 showing the tip deployment mechanism.

FIGS. 3–5 describe details of the construction of the cannula 4. FIG. 3 is an enlarged cross-sectional view of the cannula shown in FIG. 2, with the outer insulating cover partially removed, FIG. 4 is a cross-sectional view of the cannula shown in FIG. 2, taken along the line 4—4, and FIG. 5 is a cross-sectional side view of the torque tube component of the cannula shown in FIG. 3 showing the tip deployment mechanism. The cannula 4 consists of a flexible elongate torque tube or torquable tubular member 26 which extends at least over a portion of the cannula 4, and as shown in FIG. 1, extends from the steering handle 2 to the distal extremity 14. The torque tube can be formed of a suitable material such as 13 gauge thin wall stainless steel. A suitable stainless steel tube 26 has the diameter and wall thickness providing the torque capability required for the torque tube 26. For example, utilizing the same diameter, a different wall thickness ranging from 0.00711 to 0.01211 cm can be provided. The torque tube 26 can also be made of nickel-titanium alloy tubing which has greater capabilities of returning to the original or straight position than does stainless steel. A suitable nickel-titanium tubing is made of TINEL% an alloy of nickel and titanium manufactured and sold by Raychem Corporation, 300 Constitution Drive, Menlo Park, Calif. 94025. Examples of suitable torque tubes and cannulas incorporating the torque tubes in their construction are described in copending application Ser. No. 07/945,666 and the patent applications identified therein, the entire contents of all of which are hereby incorporated by reference. The torque tube can have a suitable length as determined by the length of the cannula 4.

By way of example, a catheter constructed in accordance with the present invention had a torque tube 26. A torque tube 26 having such a length is elongate and is flexible. However, to impart additional flexibility to the distal tip 28 of the torque tube 26 while retaining its high torque capabilities, the torque tube 26 is provided with at least one flexible portion 28 at the distal tip with a plurality of longitudinally spaced apart slots 30 also extending radially through the cylindrical wall of the section 28. However, in this case, the slots are not offset radially and extend substantially all the way through the circular tube except for a thin-wall portion 32 (see FIG. 4) which serves as a rib or backbone. This rib or backbone thin-wall portion 32 serves to keep the slotted section 28 unitary and also ensures that the bending in the section 28 as hereinafter described will only bend or curve in a plane which is at right angles or perpendicular to the plane of the backbone or rib 32. In order to provide different degrees of flexibility in this tip section 16, the depths of the slots 30 can be varied so as the slots become deeper, the backbone or rib 32 becomes narrower to permit greater flexibility in the backbone or rib. Conversely, if the slots are shallower, the backbone or rib 32 will become wider to provide lesser flexibility.

It should be appreciated that additional optional sections 28 could be provided in which the backbone or rib 32 could be offset as described in greater detail hereinafter with respect to FIGS. 20–23. A thin walled shrink tubing 34 made of a suitable material such as a polyolefin encapsulates the outer surface of the torque tube 28. The tubing 34 is applied by slipping it over the outer surface of the torque tube 26 and 28 and then heating the same to cause it to shrink tightly onto the torque tube 26 and 28 to be in direct contact therewith. The shrink tubing 34 serves several purposes. It serves to provide a protective wall for the catheter which encloses the torque tube 26 and 28 and provides a smooth outer surface with low friction to facilitate passage of the tube through a cystoscope or similar instrument. It also serves to prevent undue separation of the segments on the opposite sides of the slots 30.

The shrink tubing 34 is very flexible and permits desired flexing of the torque tube 16 but prevents undue bending or stress in the material of the side wall in any one slot and thereby prevents the placement of a permanent strain in any portion of the tube. In other words, the tubing 34 prevents bending or flexing of the torque tube beyond the point from which it will not yieldably return to its original configuration. The tubing 34 also serves to prevent blood or any other liquid in the lumen in which the catheter is introduced from entering into the slots 30 and causing possible clotting. The shrink tubing 34 can have an appropriate wall thickness.

An elongate tightly coiled coil spring 36 is disposed within the torque tube 28 and can extend the length of the torque tube 4. The coil spring 36 is formed of a spring steel wire rectangular in cross section. It can have suitable inside and outside diameters. The use of square wire for the coil 36 also serves to prevent collapsing of the turns of the coil during flexing of the catheter.

A second sleeve or tube formed of a flexible thin wall shrink tubing or film 38 encloses the coil 36 and the outer surfaces of the distal coil receptor 40 and proximal coil receptor 42, holding the spring 36 in place. The central passageway 44 defined by the coil 36 and the distal tip 46 direct the stylet 18 in its movement outward to the tissue to be treated.

Means is provided for causing bending of the distal extremity 16 of the cannula 4 and consists of a bendable flat or round pull wire 48 with its distal extremity 50 bonded to a distal end of the torque tube 28, for example by solder or adhesive 52. Retraction of the pull wire 48, by mechanisms disclosed in greater detail hereinafter with respect to FIGS. 9 and 1 0, forces the tip 16 to bend in the direction of the pull wire 48 as shown in FIG. 5. The proximal end 54 of the coil 36 is prevented from moving in the proximal direction by the abutment surface 56 of the proximal receptor 42 in the distal end of the support tube 58, serving as a fulcrum or pivot point for the tip.

Referring to FIG. 4, the stylet assembly enclosed within the cannula tip 16 comprises a stylet assembly within a flexible tubing 60. The assembly comprises conventional insulated thermocouple leads 62, and a stylet comprising a highly flexible RF electrode 20 enclosed within a flexible insulating sleeve 64 for longitudinal movement therein. The flexible tubing 60 can be a flexible plastic extruded with a wire braid reinforcement.

Figure 6:
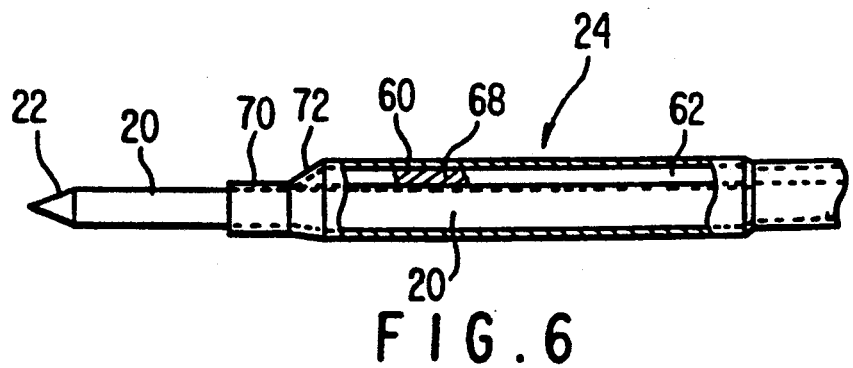
FIG. 6 is a side elevational view partially in section of distal tip of the stylet shown in FIG. 2.
Figure 7:
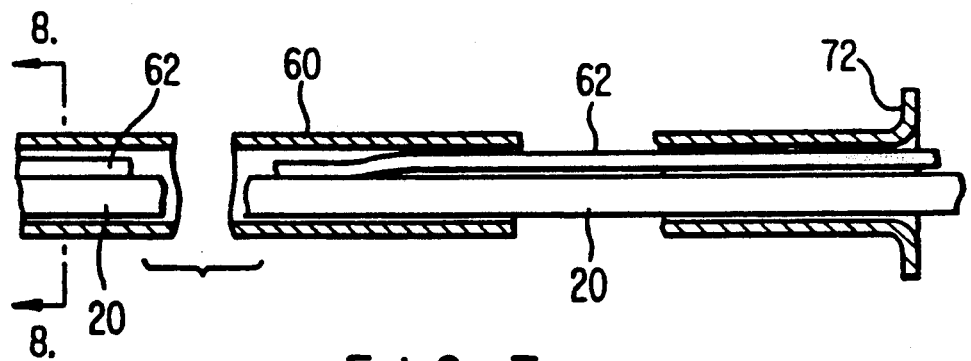
FIG. 7 shows a side elevational view in section of the intermediate portions of the control tube portion of the stylet assembly.
Figure 8:
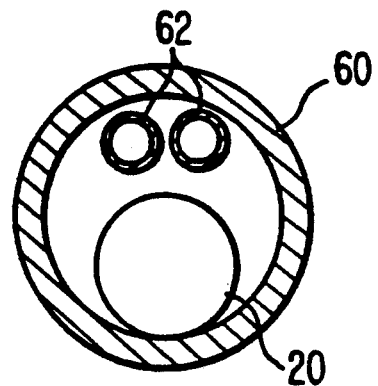
FIG. 8 is a cross-sectional view taken along the line 8—8 of FIG. 7.

FIGS. 6–8 show features of the stylet assembly 18 shown in FIG. 2. FIG. 6 is the distal tip of the stylet shown in FIG. 2. FIG. 7 shows the intermediate portions of the control tube portion of the stylet assembly. FIG. 8 is a cross-sectional view taken along the line 8—8 in FIG. 7. The distal end of the assembly comprises an RF electrode 20 having a sharpened tip 22 enclosed within an insulating sleeve 24 for longitudinal, sliding movement therein. The distal ends of the insulated thermocouple leads 62, enclosed within the control tube 60, are fused to form the thermocouple junction 68 adjacent the distal end 70 of the insulating sleeve. The distal end 70 of the sleeve assembly has a taper 72 to converge toward the electrode 20, so that the sleeve can be advanced forward along the electrode 20 through tissue layers to reduce the length of exposed electrode in the target tissue to be ablated without snagging on the intervening tissues.

Referring to FIGS. 7 and 8, the flexible outer control tube 60 encloses the stylet assembly. It must have flexibility but sufficient strength to withstand compressive forces required to advance the stylet assembly through the cannula 4 and prevent the electrode 20 and sleeve 64 from folding within the cannula when placed under compressive forces to advance the electrode 20 and insulating sleeve distal tip 70 through tissue such as the urethra to the target tissues to be ablated. The flexible control tubing 60 can be a flexible plastic extruded with a wire braid reinforcement.

Figure 9:
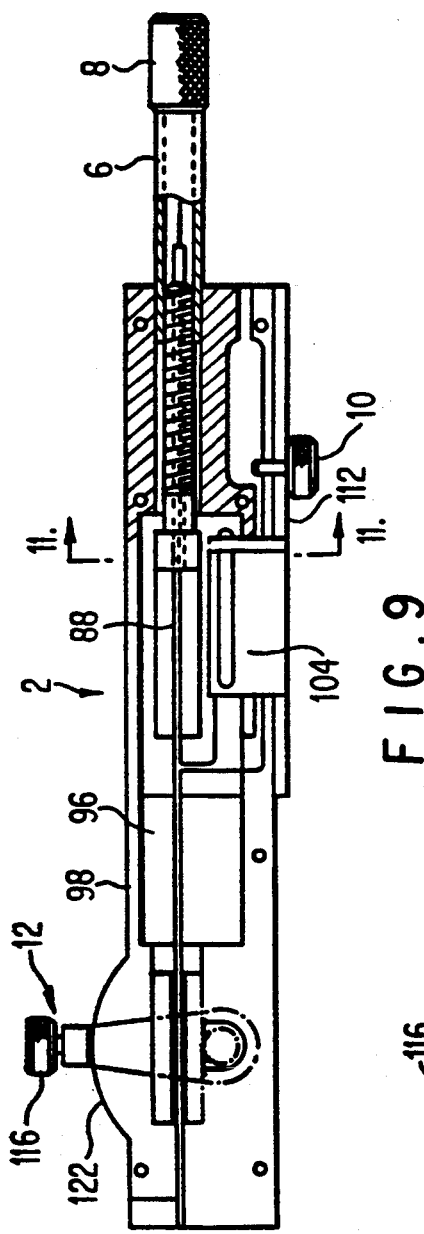
FIG. 9 is a side elevational view partially in section of the control handle of the ablation device of FIG. 1.
Figure 10:
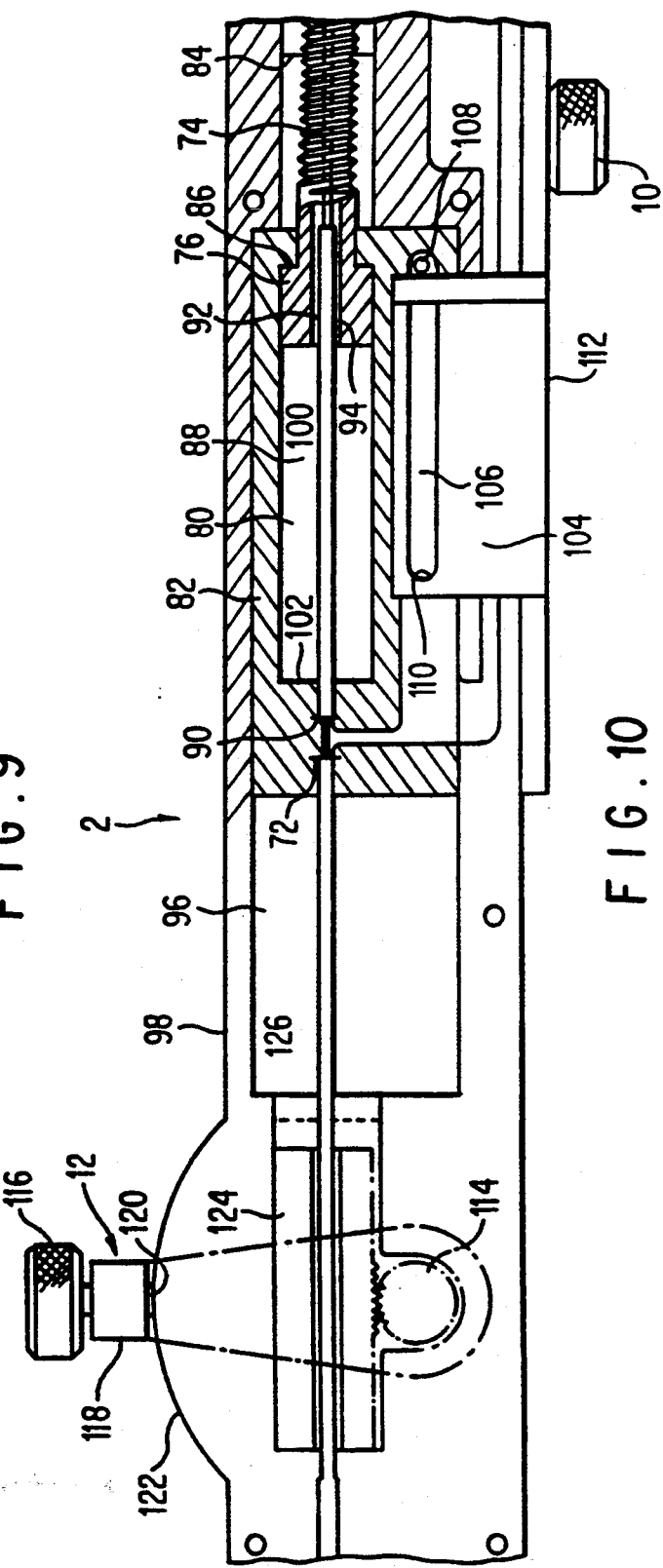
FIG. 10 is an enlarged side elevational view of the tip deployment lever and stylet deployment assembly of the control handle shown in FIG. 9.

The proximal end of the control tube 60 has a flange 72 which seats in a receptor of the control handle as described in greater detail with respect to FIGS. 9 and 10.

Figure 11:
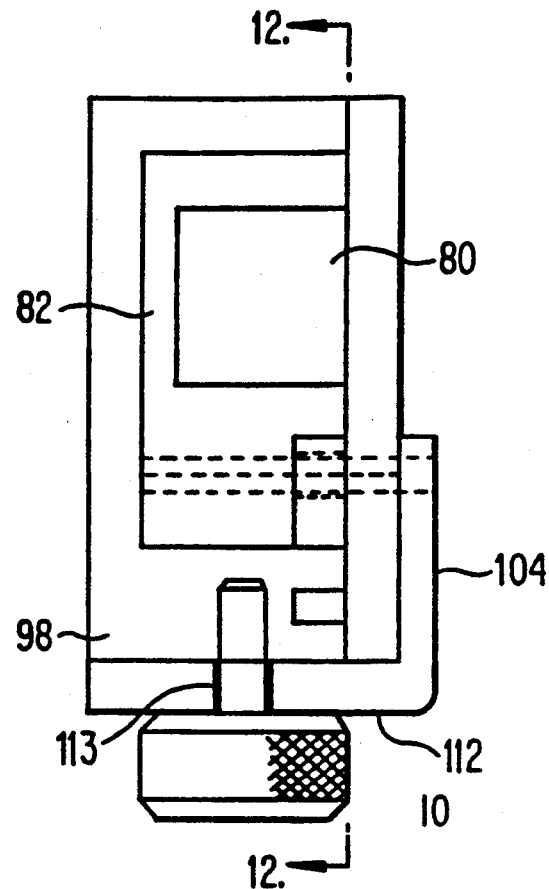
FIG. 11 is cross-sectional view taken along the line 11—11 of FIG. 9.
Figure 12:
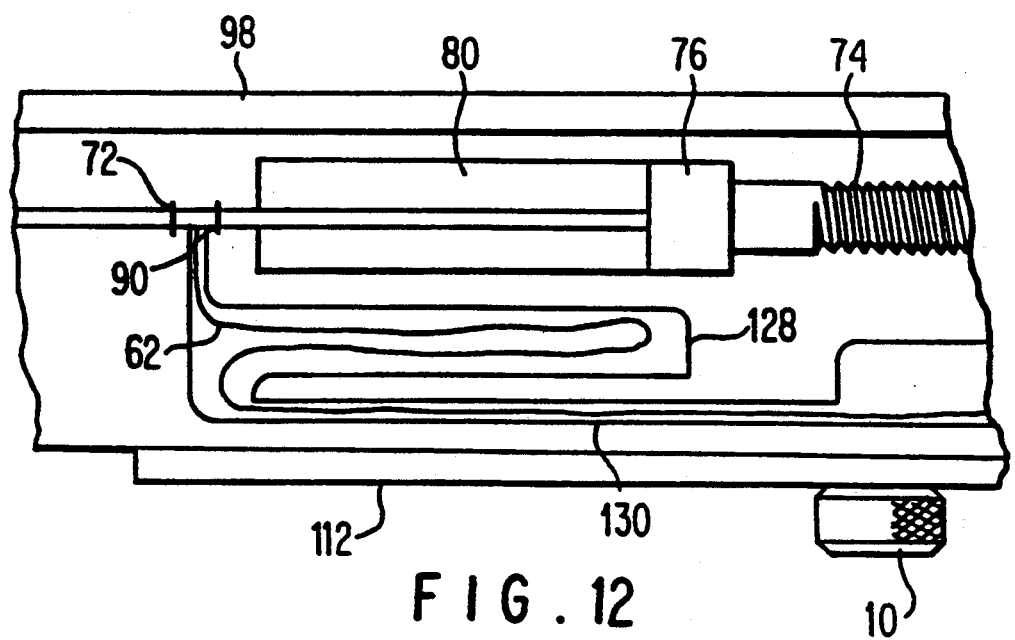
FIG. 12 is a cross-sectional view of the thermocouple wire deployment chambers, taken along the line 12—12 of FIG. 11.

FIG. 9 is a cross-sectional side view of the control handle of the ablation device of FIG. 1, and FIG. 10 is an enlarged cross-sectional side view of the tip deployment lever and stylet deployment assembly. FIG. 11 is cross-sectional view of the handle, taken along the line 11—11 of FIG. 9, and FIG. 12 is a cross-sectional view of the thermocouple wire deployment chambers, taken along the line 12—12 in FIG. 11. The manual electrode control rod 6 has a tubular portion with a circular cross-section and a threaded axial passageway which engages threaded rod 74. The distal end of the threaded rod 74 is fixedly attached to electrode slide block 76. The proximal end of the threaded rod 74 has an integral extension 78 through which the electrode 20 extends and to which the electrode 20 is fixedly attached. The electrode slide block 76 has a rectangular cross-section and is positioned for axial movement and secured against rotation about its axis within a correspondingly shaped electrode slide block slide passageway 80 in the insulating sleeve slide block housing 82. Clockwise rotation of the rod 6 about its central axis moves the rod further onto the electrode 20 and shortens the distance between the distal end 84 of the rod 6 and the electrode slide block passageway abutment surface 86 and thus shortened the distance between the electrode extension 78 and the proximal end flange 72 of the sleeve 24 (FIG. 2). This shortens the distance between the tip 22 of the electrode 20 and the distal end 70 of the sleeve 24 (FIG. 6). This thereby shortens the length of electrode 20 which extends beyond the distal end 70 of the insulating sleeve, limiting the surface of the electrode to which the tissue is exposed during ablation, and reducing the length of the ablation lesion.

Control tubing 88 is a relatively inflexible length of tubing surrounding the portion of electrode extending from the threaded rod 74 to its flanged end received in the control rod flange receiptor 90. The control tubing 88 prevents the electrode 20 from folding when it is placed under compressive forces when the slide block 76 is moved forward (to the left in the distal direction) within the slide passageway 80. The proximal end 92 of the control tubing 88 extends into an axial passageway 94 extending through the distal portion of the threaded rod 74.

The insulating sleeve block housing 82 thus has a receptor in which the flanged proximal end 72 of the insulating sleeve is secured. The insulating sleeve block housing 82 has a rectangular cross-section and is positioned for axial movement and secured against rotation about its axis within a correspondingly shaped sleeve slide block slide passageway 96 in the handle housing 98. Sliding movement of the sleeve block housing 96 in the distal direction (to the left in the figure) advances the sleeve outward from the end of the torque tube.

Longitudinal movement of the rod 6 in the distal direction (to the left in the figure) causes slide block 76 to slide in the passageway 80 until its distal face 1 00 abuts the abutment surface 102 at the distal end the passageway 80 and advances the electrode 20 to its final position with respect to the sleeve. Further longitudinal movement of the knurled rod in the distal direction moves the sleeve block housing 82 in the distal direction, causing the advancement of the electrode 20 and sleeve 24 as a unit from the distal end of the cannula.

The maximum longitudinal movement of the sleeve slide block in the distal direction can be preset by adjustment of the slide limit plate 104 with the slot 106. Pin 108 extending from the side of the sleeve slide block 82 engages and slides down slot 106 in the slide limit plate 104 until it hits the slot abutment surface 110. The slide limit plate 104 is secured to bottom plate 112 and secured to the handle housing 98 by knurled hand screw 10. Knurled knob 10 extends through a slide plate slot 113 in the plate 112 and threadingly engages the bottom of the handle housing 98. Advancement of the knob 10 locks the plate 112 into position against the bottom of the housing 98, and retracting (loosening) the knob 10 permits movement of the plate 104 to the desired setting. The longitudinal position of the slide plate 104 is manually adjusted to limit the extension of the electrode 20 and sleeve tip 70 into the tissue and secured in place on the housing by tightening the hand screw 10.

The proximal end of pull wire 48 (FIG. 5) is controlled by the pull wire control lever 12. The control lever 12 is secured to pinion 114 and pivots with the pinion about the central axis thereof. Pull wire control lever hand screw 116 threadingly engages lever plate 118. Advancement of the hand screw 116 in the lever plate 118 causes the screw tip 120 to abut the curved housing surface 122, fixing the position of the lever. Rack 124 is positioned for longitudinal movement in rack receptor 126 of the handle housing 98. The rack 124 is secured to the distal end of the pull wire 48. The teeth of rack 124 engage the teeth of the pinion 114 and is caused to move in the proximal direction by pivotal movement of the control lever 12 in the counter-clockwise or distal direction, thus retracting the pull wire and causing curvature of the tip 14 as shown in FIG. 5. When the desired tip curvature has been achieved, the hand screw 116 is advanced against the surface 122 to fix the tip curvature during the subsequent steps of the procedure. After the ablation has been completed and the stylet retracted to a position within the cannula, the set screw is retracted, and the lever is moved in the proximal direction, permitting return of the flexible tip to a straightened or non-curved orientation.

Insulated thermocouple wire leads 62 exit between flange receptors 72 and 90, are looped from one end to the other and then back in thermocouple lead cavity 128 to provide the thermocouple lead length required when the stylets are fully extended. The thermocouple leads 62 then pass through a thermocouple passageway 130 toward the connection to a control console (not shown).

In one mode of operation of the device of this invention with a cystoscope, the rod 8 is turned to set the desired exposure of the electrode tip 22. The cystoscope is advanced up the urethra until its end is positioned in a selected location within the prostate. The cannula 4 is then advanced until the flexible tip 14 is positioned at the distal end of the cystoscope. The pull wire lever 12 is rotated toward the distal end until the desired curvature of the tip 14 is achieved, that is, positioned to direct the stylet outward through the urethral wall at the desired angle to the target tissue to be ablated. The rod 6 is then pushed in the distal direction until abutment of the slide surface 100 with the abutment surface 102 occurs. Subsequent distal movement of the rod 6 pushes the stylet outward through the urethral wall and to the desired depth in the prostate. RF current is then passed through the electrode to the exposed distal surface thereof, through the surrounding prostate tissue and to an indifferent skin surface electrode. Passage of the RF current is continued until the desired ablation is achieved, the circuit to the electrode is opened, the rod 6 is pulled in the proximal direction to withdraw the electrode and sleeve from the tissue until it is enclosed in the cannula. The pull wire lever 12 is pulled or rotated in the proximal direction to straighten the tip 14. The cannula 4 and cystoscope are then moved to a different location in the urethra to form another lesion or withdrawn from the urethra.

Figure 13:
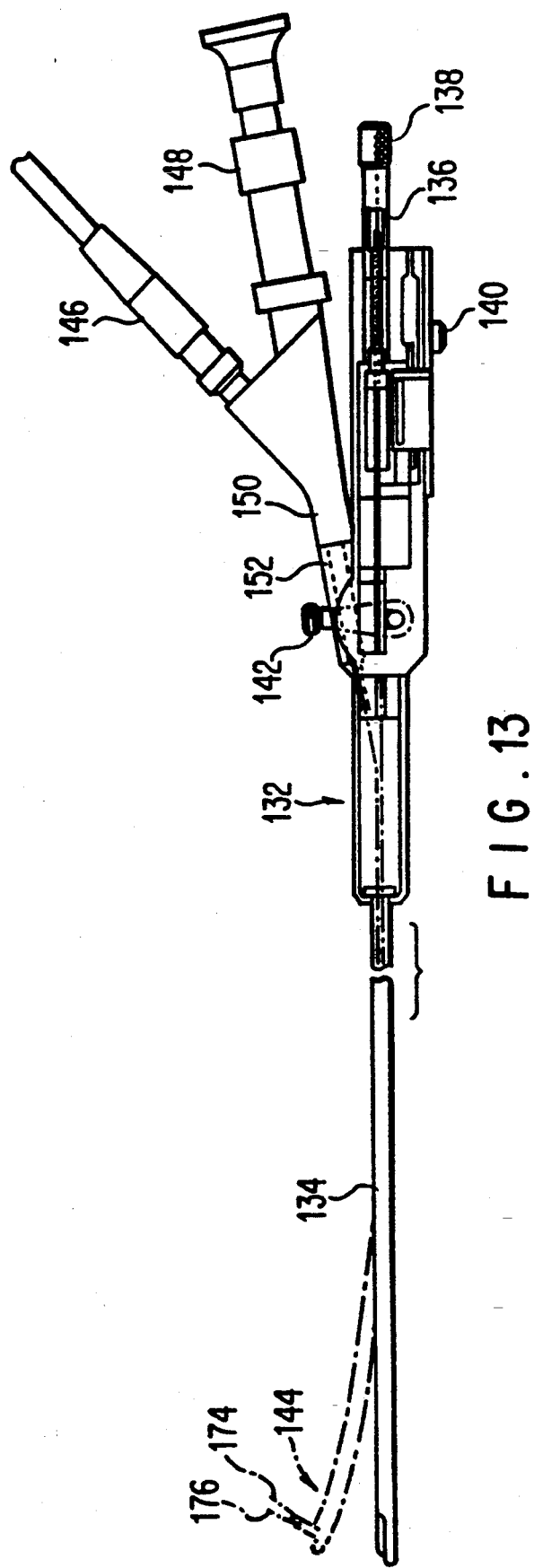
FIG. 13 is side elevational view partially in section of an alternate embodiment of the ablation device of this invention with an optic viewing capability.

FIG. 13 is a side view of an alternative embodiment of this invention with an optic viewing capability. The control handle 132 supports a flexible ablation cannula 134 extending in the distal direction therefrom. A manual electrode control rod 136 with a knurled tip 138 extends from the handle 132 in the proximal direction for advancing and retracting the RF electrode component of the stylet as will be described in greater detail hereinafter. Manual stylet control knob 140 extends from the bottom of handle advance and retract the stylet as described in greater detail hereinafter. A cannula tip deployment lever 142 is mounted on the top of the handle 132. The distal tip 144 of the cannula is flexible. Movement of the lever 142 in the proximal direction (to the right in the figure, toward the user) deploys the tip 144 in a direction which is off-axis from the central axis of the cannula. The external optic viewing components are those conventionally employed with cystoscopes and similar viewing devices including a light source 146, adjustable lens housing 148, bridge support 150 for these elements, and a housing receptor 152 into which the bridge support 150 is supported.

Figure 14:
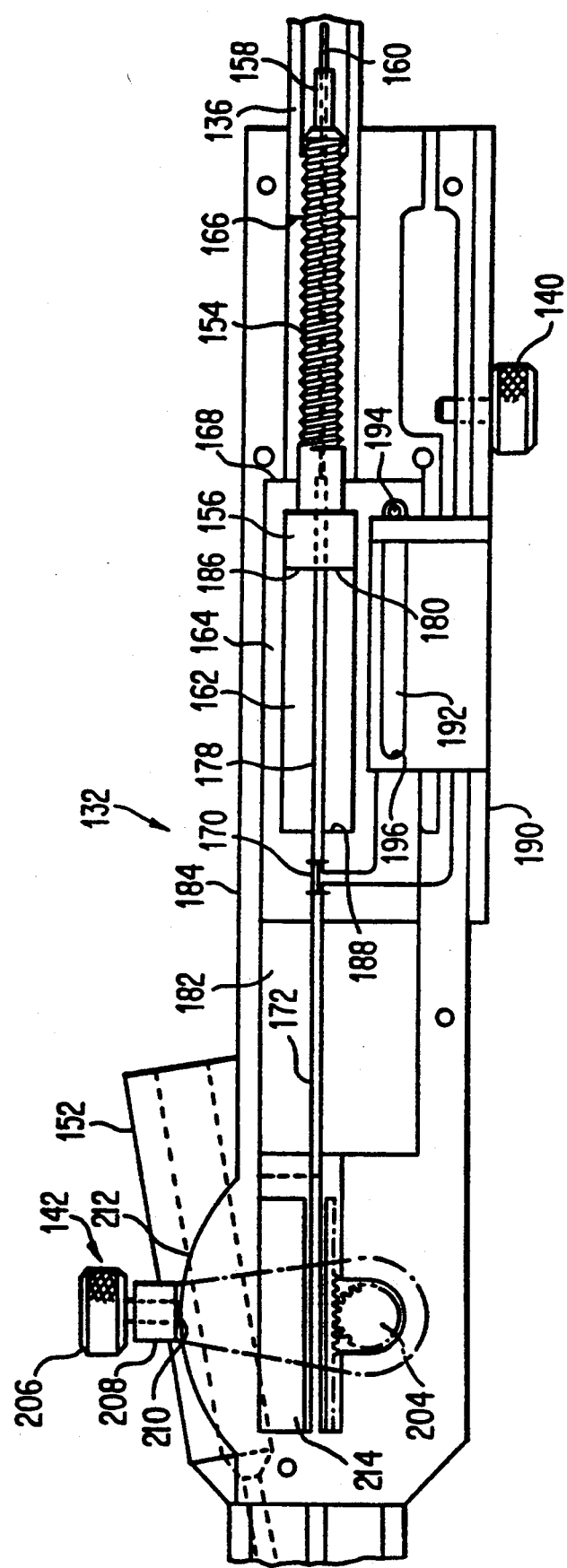
FIG. 14 is an enlarged side elevational view of the control handle for the ablation device of FIG. 13 with the optic viewing capability removed.

FIGS. 14–20 disclose details of ablation device embodiment shown in FIG. 13. FIG. 14 is a cross-sectional side view of the control handle for the ablation device of FIG. 13 with the optic components removed.

In this embodiment, the components of the embodiment shown in FIG. 1 can be duplicated in mirror image for example, the left side components being shown in FIG. 14. The manual electrode control rod 136 has a tubular portion with a circular cross-section and a threaded axial passageway which engages threaded rod 154. The distal end of the threaded rod 154 is fixedly attached to electrode slide block 156. The proximal end of the threaded rod 154 has an integral extension 158 through which the electrode 160 extends and to which the electrode 160 is fixedly attached. The electrode slide block 156 has a rectangular cross-section and is positioned for axial movement and secured against rotation about its axis within a correspondingly shaped electrode slide block slide passageway 162 in the insulating sleeve slide block housing 164. Clockwise rotation of the rod 136 about its central axis retracts the electrode and shortens the distance between the distal end 166 of the threaded rod and the proximal end 168 of the insulating sleeve slide block housing 164 and proximal end flange 170 of the insulating sleeve 172. This shortens the distance between the distal tip of the electrode 160 and the distal end 170 of the sleeve 172. This thereby shortens the length of distal electrode length 174 which extends beyond the distal end 176 (FIG. 13) of the insulating sleeve 172, limiting the surface of the electrode to which the tissue is exposed during ablation, and reducing the length of the ablation lesion.

Control tubing 178 is a relatively inflexible length of tubing surrounding the portion of electrode extending from the threaded rod 154 to the sleeve receptor 170. The control tubing prevents the electrode from folding when it is placed under compressive forces when the slide block 164 is moved forward (to the left in the distal direction) within the slide passageway 162. The distal end of the control tube 174 has a flange terminus which is secured in a control tube flange receptor 170. The proximal end of the control tubing 174 extends into an axial passageway 180 in the distal portion of the threaded rod 154.

The insulating sleeve block housing 164 thus has a receptor in which the flanged proximal end of the insulating sleeve is secured. The insulating sleeve block housing 164 has a rectangular cross-section and is positioned for axial movement and secured against rotation about its axis within a correspondingly shaped sleeve slide block slide passageway 182 in the handle housing 184. Sliding movement of the sleeve block housing 164 in the distal direction (to the left in the figure) advances the sleeve outward from the end of the torque tube.

Longitudinal movement of the knurled rod 136 in the distal direction (to the left in the figure) causes it to slide in the passageway 162 until its distal face 186 abuts the abutment surface 188 at the distal end of the passageway 162 and advances the electrode 160 to its final position with respect to the sleeve. Further longitudinal movement of the knurled rod in the distal direction moves the sleeve block housing 164 in the distal direction, causing the advancement of the electrode 160 and sleeve 172 as a unit from the distal end of the cannula.

Longitudinal movement of the sleeve slide block in the distal direction can be preset by adjustment of the slide limit plate 190 with the slot 192. Pin 194 extending from the side of the sleeve slide block 164 engages and slides down slot 192 in the slide limit plate 190 until it hits the slot abutment surface 196.

Figure 15:
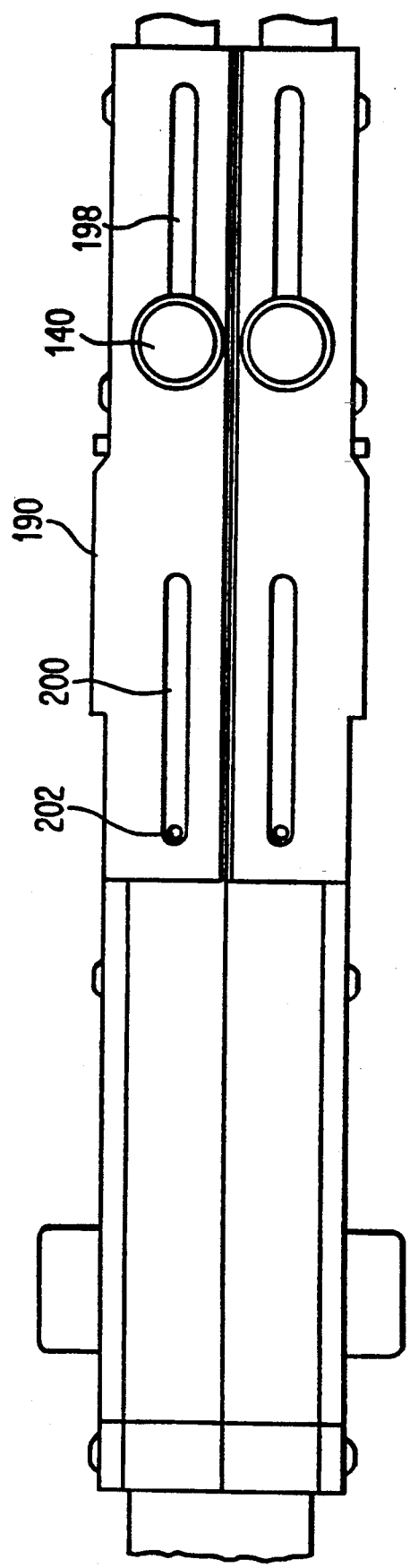
FIG. 15 is a bottom plan view of the control handle for the ablation device of FIG. 13.

Referring to FIG. 15, a bottom view of the control handle for the ablation device of FIG. 13 is shov n. Knurled knob 140 extends through a knob slot 198 in the bottom of plate 190 and threadingly engages the bottom of the handle housing 184. Advancement of the knob 140 locks the plate 190 into position against the bottom of the housing, and retracting (loosening) the knob 140 permits movement of the plate 190 to the desired setting. The bottom section of plate 190 has an additional slot 200 and pin 202 to secure the plate movement. The longitudinal position of the slide plate 190 is adjusted to limit the extension of the electrode ( 160 in FIG. 14, 174 in FIG. 13) and sleeve ( 172 in FIG. 14, 176 in FIG. 13) into the tissue and secured in place on the housing by tightening the hand screw 140.

A pull wire (not shown) connected to the distal end of the catheter 134 is controlled by the pull wire control lever 142 as described with respect to FIG. 10. The control lever 142 is secured to pinion 204 and pivots with the pinion about the central axis thereof. Pull wire control lever hand screw 206 threadingly engages lever plate 208. Advancement of the hand screw 206 in the lever plate 208 causes the screw tip 210 to abut the curved housing surface 212, fixing the position of the lever. Rack 214 is positioned for longitudinal movement in a rack receptor in the handle housing. The rack 21 4 is secured to the distal end of the pull wire (not shown). The teeth of rack 204 engage the teeth of the pinion 214 and are caused to move in the proximal direction by pivotal movement of the control lever 208 in the counter-clockwise or distal direction, thus retracting the pull wire and causing curvature of the catheter tip 144 as shown in FIG. 13. When the desired tip curvature has been achieved, the hand screw 206 is advanced against the surface 21 2 to fix the tip curvature during the subsequent steps of the procedure. After the ablation has been completed and the style retracted to a position within the cannula, the set screw is retracted, and the lever is moved in the proximal direction, permitting return of the flexible tip to a straightened or non-curved orientation.

FIG. 16 is a top view of the control handle for the ablation device of FIG. 13, and FIG. 17 is a cross-sectional view of the control handle of FIG. 16, taken along the line 17—17, showing other views of the device and its internal construction.

FIG. 18 is an enlarged cross-sectional side view of the optics assembly of the ablation device of FIG. 13 with flushing liquid connection 216 shown. The flushing liquid connection 21 6 supplies liquid to flush to distal end of the fiber optic to maintain it free from debris and permitting continuing viewing. The fiber optic 218 extends through flushing liquid connector housing 220, and O-rings 222 establish a seal between the flushing liquid housing 220 and the external surface of the optic 218, preventing escape of flushing liquid into the external housing 224. The liquid is directed between the outer surface of the optic 218 and its surrounding sleeve or tube 226.

FIG. 19 is a cross-sectional view of the distal end of the handle shown in FIG. 18, taken along the line 19—19. The stylets 228 and 230 extend with the fiber optic assembly 232 through the terminal block 234.

FIG. 20 is a cross-sectional view of the cannula shown in FIG. 18, taken along the line 20—20. In this view, the relative positions of the stylets 228 and 230 and fiber optic 232 in the catheter 134 is shown.

The embodiment of this invention shown in FIGS. 13-20 is suitable for use as a complete unit and does not require a cystoscope.

FIG. 21 is a cross-sectioned side view of an alternate torque tube assembly without the insulating outer cover, and FIG. 22 is a cross-sectional view of the torque tube shown in FIG. 21. This assembly can be used with any of the embodiments of this invention to provide a flexible catheter (FIG. 1) or cannula (FIG. 13). For purposes of clarity, this torque tube component will be described with respect to the embodiment of FIG. 13. The cannula 134 consists of a flexible elongate torque tube or torquable tubular member 136 which extends at least over a portion of the cannula, and as shown in FIGS. 1 and 13, extends from a steering handle to a distal extremity. The torque tube can be formed of a suitable material such as 13 gauge thin wall stainless steel. It should be appreciated that it is within the scope of this invention to utilize torque tubes of various diameters and wall thicknesses depending upon the torque capability required for the torque tube 236. For example, utilizing the same diameter, a different wall thickness ranging from 0.00711 to 0.01211 cm can be provided. The torque tube 236 can also be made of nickel-titanium alloy tubing which has greater capabilities of returning to the original or straight position than does stainless steel. A suitable nickel-titanium tubing is made of TINEL ®, an alloy of nickel and titanium manufactured and sold by Raychem Corporation, 300 Constitution Drive, Menlo Park, Calif. 94025.

By way of example, a catheter constructed in accordance with the present invention had a torque tube 236 having a length of __cm. A torque tube 236 having such a length is elongate and is flexible. However, to impart additional flexibility to the distal tip 144 of the torque tube 236 while retaining its high torque capabilities, the torque tube 236 is provided with at least one flexible portion 238 at the distal tip with a plurality of longitudinally spaced apart slots 240 also extending radially through the cylindrical wall of the section 238. However, in this case, the slots are not offset radially and extend substantially all the way through the circular tube except for a thin-wall portion 242 (see FIG. 22) which serves as a rib or backbone. This rib or backbone thin-wall portion 242 serves to keep the slotted section 238 unitary and also ensures that the bending in the section 238 as hereinafter described will only bend or curve in a plane which is at right angles or perpendicular to the plane of the backbone or rib 242. In order to provide different degrees of flexibility in this tip section, the depths of the slots 240 can be varied so as the slots become deeper, the backbone or rib 242 becomes narrower to permit greater flexibility in the backbone or rib. Conversely if the slots are shallower, the backbone or rib 242 will become wider to provide lesser flexibility. The distance (width of ribs 244) between each slot 240 in a flexible portion can be defined as the pitch.

In this embodiment, the bottom of the slots have an L-shaped portion 246 to increase flexibility of the tip while retaining resistance to twisting or bending in an undesired plane. A thin walled shrink tubing made of a suitable material such as a polyolefin encapsulates the outer surface of the torque tube 238 as described above with respect to FIG. 3. Pull wire 248 extends through the torque tube and is secured in recess 250 at the distal end thereof. Retraction of the pull wire 248 effects curvature in the torque tube as described above with respect to FIG. 5.

Figure 23:
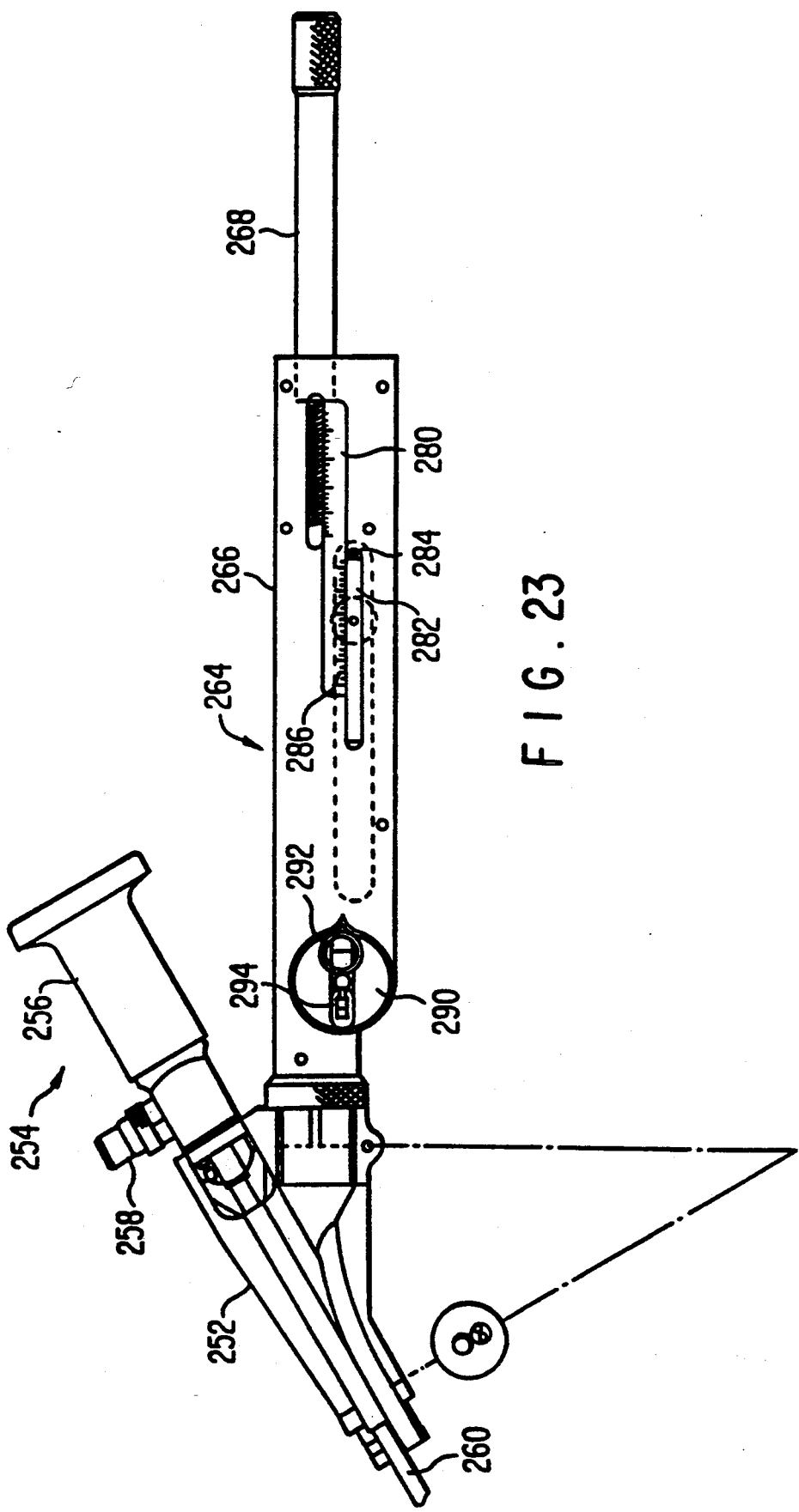
FIG. 23 is a side elevational view of another embodiment of this invention with two separate steerable tips for use with a special bridge construction and a standard cystoscope.

FIG. 23 is a side view of an embodiment of this invention with two separate stearable tips for use with a special bridge construction and a standard cystoscope. FIG. 24 is a top view thereof. FIG. 25 is a cross-sectional view taken along the line 25—25 of FIG. 24. In this embodiment, the bridge 252 is designed to fit into a bridge receptor (not shown) in a cystoscope. FIG. 26 is a bottom view thereof. FIG. 27 is a cross-sectional side view of the handle showing its essential components. Bridge 252 supports a conventional optic viewing assembly 254 including a conventional, focusing lens 256, light source connector 258 and fiber optic assembly 260. Bridge 252 also includes a receptor for the distal projection 262 of the control handle 264.

The control handle 264 combines the same components described above with respect to FIG. 9-20 in a slightly different configuration, and reference to these figures and the supporting descriptions should be made for features of this embodiment which are not specifically described hereinbelow. As with the embodiment of FIGS. 13-20, this embodiment comprises two essentially identical, mirror image units, each operating a single cannula-stylet combination. The housing 266 has control rods 268 extending from its proximal end threadingly engaging the threaded rods 270.

Referring particularly to FIG. 27, the threaded rods 270 are connected to electrode control blocks 272 sliding in slide block passageways 274 in the respective sleeve control slide blocks 276. The sleeve control slide blocks 276 are positioned in slide passageways 278. The position of the threaded rods 270 are adjusted by rotation of the rods 268 to a setting observed with respect to the distal scales 280. The stops for the internal slide blocks 276 include slide slots 282 and pins 284. The position of the slide blocks are adjusted to a setting observed with respect to the proximal scales 286, and the knobs 288 is independently advanced to secure each in the preselected position.

The pull wire control lever of FIGS. 10 and 18 are replaced by wheels 290 and 291, each having a threaded knob 292 and a thumb projection 294 displaced from the central axis thereof on opposite sides of the wheel. The axle of each wheel is fixed to a respective rack 296 engaging a pinion 298. Rotation of the wheel in a direction which causes movement of the pinion 298 in the proximal direction (to the right in FIG. 27) retracts the pull wire (not shown) attached thereto, causing the distal tip of the respective cannula to bend upward as shown in FIG. 1.

The distal end of the handle has a projection which is received in a correspondingly shaped receptor in the bridge 252. Knurled wheel 300 has internal threads which engage external threads on the bridge to secure the handle to the bridge.

Although preferred embodiments of the subject invention have been described in some detail, it is understood that obvious variations can be made without departing from the spirit and the scope of the invention as defined by the appended claims.

We claim:

1. A medical probe for the treatment by radio frequency ablation of a target volume in tissue of a prostate of a human male having a bladder with a base and a penis with a urethra therein formed by a urethral wall extending into the base of the bladder along a longitudinal axis with the tissue of the prostate surrounding the urethra near the base of the bladder comprising an elongate probe member having proximal and distal extremities and being sized so that it can be introduced into the urethra, said elongate probe member having a passage extending from the proximal extremity to the distal extremities, first and second guide cannulas mounted side by side in the passage of the elongate probe member and having proximal and distal extremities with the distal extremity of the guide cannulas being in the vicinity of the distal extremity of the elongate probe member, each of said guide cannulas having a lumen extending therethrough from the proximal extremity to the distal extremity, a radio frequency conductive electrode disposed in each lumen, an insulating sleeve coaxially disposed on each of said radio frequency electrodes, a control handle secured to the proximal extremity of the elongate probe member and means carried by the control handle and secured to the radio frequency electrode and the insulating sleeve in each lumen whereby the radio frequency electrode and the insulating sleeve in each lumen can be advanced and retracted.

2. A probe as in claim 1 together with means carried by the handle for causing bending of the distal extremity of each of the first and second guide cannulas to thereby control the direction of penetration of the radio frequency electrode through the urethral wall and into the tissue of the prostate.

3. A probe as in claim 1 wherein the distal extremity of each of the guide cannula is provided with a cylindrical wall, said cylindrical wall having at least a portion thereof containing a plurality of longitudinally spaced apart circumferentially extending slots subtending less than 360 degrees formed therein, said slots facilitating bending of the guide cannula in said flexibe portion of the distal extremity of the guide cannula.

4. A probe as in claim 3 wherein said slots are circumferentially aligned to provide a backbone extending longitudinally of the flexible portion so as to permit bending in only a single direction.

5. A probe as in claim 3 wherein said flexible portion can be bent through an angle at least approximating 90 degrees.

6. A probe as in claim 1 together with means carded by the control handle for pre-adjusting on the control handle the maximum distance the radio frequency electrode in each of the lumens can be extended distally.

7. A probe as in claim 6 together with means carried by the control handle for pre-adjusting on the control handle the amount of extension of the insulating sleeve.

8. A probe as in claim 7 wherein said means carried by the handle for adjusting the position of the radio frequency electrode and the position of the insulating sleeve includes means for causing relative movement between the insulating sleeve and the radio frequency electrode in each lumen so that a preselected length of the radio frequency electrode in each lumen can be exposed in tissue of the prostate.

9. A probe as in claim 1 together with a cystoscope carried by the control handle and having a distal extremity in the vicinity of the distal extremity of the elongate probe member.

10. A medical probe for the treatment by radio frequency ablation of a target volume in tissue of a prostate of a human male having a bladder with a base and a penis with a urethra therein formed by a urethral wall extending into the base of the bladder along a longitudinal axis with the tissue of the prostate surrounding the urethra near the base of the bladder comprising an elongate probe member having proximal and distal extremities and being sized so that it can be introduced into the urethra, said elongate probe member having a passage extending from the proximal extremity to the distal extremity, a guide cannula mounted in the passage of the elongate probe member and having proximal and distal extremities with the distal extremity of the guide cannula being in the vicinity of the distal extremity of the elongate probe member, said guide cannula having a lumen extending therethrough from the proximal extremity to the distal extremity, a radio frequency conductive electrode disposed in said lumen, an insulating tube coaxially disposed on said radio frequency electrode, a control handle secured to the proximal extremity of the elongate probe member, means carried by the control handle and secured to the radio frequency electrode and the insulating sleeve in the lumen whereby the radio frequency electrode and the insulating sleeve thereon can be advanced and retracted, means for causing bending of the distal extremity of the guide cannula to thereby control the direction of penetration of the radio frequency electrode through the urethral wall and into tissue of the prostate, the distal extremity of the guide cannula being provided with a cylindrical wall, said cylindrical wall having at least a portion thereof containing a plurality of longitudinally spaced apart circumferentially extending slots subtending less than 360 degrees formed therein, said slots facilitating bending of the guide cannula in said portion of the distal extremity of the guide cannula.

11. A probe as in claim 10 wherein said slots are circumferentially aligned to provide a backbone extending longitudinally of the flexible portion so as to permit bending in only a single direction.

12. A medical device for the treatment by radio frequency ablation of a target volume in tissue of a prostate of a human male having a bladder with a base and a penis with a urethra therein formed by a urethral wall extending into the base of the bladder along a longitudinal axis with the tissue of the prostate surrounding the urethra near the base of the bladder comprising an elongate probe member having proximal and distal extremities and having a passage therein extending from the proximal extremity to the distal extremity, said elongate probe member being sized so that it can be introduced into the urethra, first and second guide cannulas mounted side by side in the passage of the elongate probe member and having proximal and distal extremities with portions between the proximal and distal extremities, means for fastening together said portions so that they are disposed side by side, each of said guide cannulas having a lumen extending therethrough from the proximal extremity to the distal extremity, a radio frequency conductive electrode disposed in each lumen, an insulating sleeve coaxially disposed on each of said radio frequency electrodes, a handle secured to the proximal extremities of the first and second guide cannulas and means carried by the handle and secured to the radio frequency electrode and the insulating sleeve in each lumen whereby the radio frequency electrode and the insulating sleeve in each lumen can be advanced and retracted with respect to the guide cannula.

13. A device as in claim 12 together with means carried by the handle for causing bending of the distal extremity of each of the first and second guide cannulas to thereby control the direction of penetration of the radio frequency electrode through the urethral wall and into the tissue of the prostate.

14. A device as in claim 13 wherein the distal extremity of each of the guide cannulas is provided with a cylindrical wall, said cylindrical wall having at least a portion thereof containing a plurality of longitudinally spaced apart circumferentially extending slots subtending less than 360 degrees formed therein to provide a flexible portion, said slots facilitating bending of the guide cannula in said flexible portion of the distal extremity of the guide cannula.

15. A device as in claim 14 wherein said slots are circumferentially aligned to provide a backbone extending longitudinally of the flexible portion so as to permit bending in only a single direction.

* * * * *